US012617766B2

(12) United States Patent
Zhang et al.

(10) Patent No.: US 12,617,766 B2
(45) Date of Patent: May 5, 2026

(54) CRYSTAL FORM OF THIOPHENE DERIVATIVE AND PREPARATION METHOD THEREFOR

(71) Applicant: TONGHUA DONGBAO PHARMACEUTICAL CO., LTD., Jilin (CN)

(72) Inventors: Yang Zhang, Shanghai (CN); Wentao Wu, Shanghai (CN); Zhixiang Li, Shanghai (CN); Wenyuan Zhu, Shanghai (CN)

(73) Assignee: TONGHUA DONGBAO PHARMACEUTICAL CO., LTD., Jilin (CN)

( * ) Notice: Subject to any disclaimer, the term of this patent is extended or adjusted under 35 U.S.C. 154(b) by 367 days.

(21) Appl. No.: 18/556,896

(22) PCT Filed: Apr. 21, 2022

(86) PCT No.: PCT/CN2022/088295
§ 371 (c)(1),
(2) Date: Oct. 24, 2023

(87) PCT Pub. No.: WO2022/228280
PCT Pub. Date: Nov. 3, 2022

(65) Prior Publication Data

US 2024/0239763 A1 Jul. 18, 2024

(30) Foreign Application Priority Data

Apr. 29, 2021 (CN) ......................... 202110472705.3
Sep. 18, 2021 (CN) ......................... 202111112439.X

(51) Int. Cl.
*C07D 333/72* (2006.01)
*A61K 31/381* (2006.01)

(52) U.S. Cl.
CPC .......... *C07D 333/72* (2013.01); *A61K 31/381* (2013.01)

(58) Field of Classification Search
CPC ..... C07D 333/72; A61K 31/381; A61P 19/06; A61P 19/02; C07B 2200/13
See application file for complete search history.

(56) References Cited

U.S. PATENT DOCUMENTS 10,266,496 B2 4/2019 Yang et al.
2018/0230102 A1 8/2018 Yang et al.
(Continued)

FOREIGN PATENT DOCUMENTS

CN 106478500 A 3/2017
EP 0189596 A1 8/1986
(Continued)

OTHER PUBLICATIONS

Sep. 10, 2024 1st Japan Office Action issued in Japanese Patent Application No. 2023-566003.
(Continued)

*Primary Examiner* — Rebecca L Anderson
*Assistant Examiner* — David M Shim
(74) *Attorney, Agent, or Firm* — Houston Beshining Law Office PLLC; Liangang Ye

(57) ABSTRACT

Provided are a crystal form of a compound represented by formula (I) and a preparation method therefor.
(Continued)

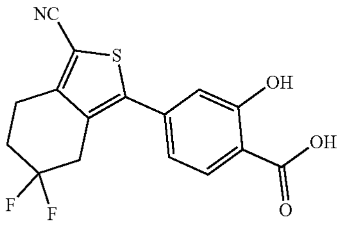

(I)

20 Claims, 7 Drawing Sheets

(56) References Cited

U.S. PATENT DOCUMENTS

| | | | |
|---|---|---|---|
| 2020/0140423 | A1 | 5/2020 | Wang et al. |
| 2023/0322703 | A1 | 10/2023 | Zhang et al. |

FOREIGN PATENT DOCUMENTS

| | | | | | |
|---|---|---|---|---|---|
| EP | 3712148 | A1 | 9/2020 | | |
| JP | 2018532698 | A | 11/2018 | | |
| JP | 2019519606 | A | 7/2019 | | |
| WO | 2010044403 | A1 | 4/2010 | | |
| WO | WO 2021/083319 | A1 * | 5/2021 | ............. | C07D 33/70 |

OTHER PUBLICATIONS

Jun. 21, 2022 International Search Report issued in International Patent Application No. PCT/CN2022/088295.
Jun. 21, 2022 Written Opinion of the International Searching Authority issued in International Patent Application No. PCT/CN2022/088295.
English Translation of Priority Document CN 202111112439X.
English Translation of Priority Document CN 2021104727053.
Sarma B et al. Solid formation of pharmaceuticals: Polymorphs, salt and cocrystals. Korean J.Chem.Eng., 2011, 28 (2), p. 315-322.
Narayan Variankaval; et al.: "From form to function: Crystallization of active pharmaceutical ingredients", AlChE, 2008, vol. 54(7), p. 1682-1688.
Jun. 2, 2024 First Office Action issued in Russia Patent Application No. 2023130956.
Mar. 21, 2025 extended European search report issued in European Patent Application No. 22794751.2.
Apr. 14, 2025 First Office Action issued in Chinese Patent Application No. 202280015619.2.
Apr. 11, 2025 First Search Report issued in Chinese Patent Application No. 202280015619.2.
Sep. 16, 2025 a Communication under Article 94(3) EPC from the European Patent Office (EPO) for European Patent Application No. 22794751.2.

* cited by examiner

CRYSTAL FORM OF THIOPHENE DERIVATIVE AND PREPARATION METHOD THEREFOR

The present application is a National Stage of International Application No. PCT/CN2022/088295, filed on Apr. 21, 2022, which claims priorities of the Chinese Patent Application No. CN202110472705.3 filed on Apr. 29, 2021, the Chinese Patent Application No. CN202111112439.X filed on Sep. 18, 2021.

TECHNICAL FIELD

The present disclosure relates to a crystal form of a thiophene derivative and a preparation method thereof, specifically to a crystal form of formula (I) and a preparation method thereof.

BACKGROUND

Gouty arthritis is a common and complex type of arthritis. When the concentration of uric acid in the human blood exceeds 7 mg/dL, uric acid is deposited in the joints, cartilage, and kidneys in the form of monosodium salt, leading to an overactive (sensitive) immune system, thus causing painful inflammation. The common areas attacked are the metatarsophalangeal joint, ankle joint, knee joint, etc. Hyperuricemia is the pathological basis of gouty arthritis. Hyperuricemia refers to a disorder in the metabolism of purine substances within the human body, resulting in an increase in uric acid synthesis or a decrease in its excretion, leading to an abnormally high level of uric acid in the blood. Internationally, the standards for diagnosis of hyperuricemia (HUA) are defined as: under normal purine dietary conditions, fasting blood uric acid levels measured twice on different days exceed 400 μmol/L (6.8 mg/dL) for men and 360 μmol/L (6 mg/dL) for women. It can be categorized into three types, underexcretion of uric acid, overproduction of uric acid, or mixed type. Clinical research indicates that 90% of primary hyperuricemia falls under the category of underexcretion of uric acid.

Hyperuricemia is inextricably linked with gout and is an independent risk factor for metabolic diseases [such as diabetes, metabolic syndrome (MS), hyperlipidemia], chronic kidney disease, cardiovascular disease, and stroke. Therefore, reducing the level of uric acid in the human body can be conducive not only to the treatment or prevention of hyperuricemia and gout but also to lowering the risk of other complications associated with hyperuricemia.

There are two sources of purines within the human body: endogenous purines, originating from self-synthesis or nucleic acid breakdown (approximately 600 mg/d), and exogenous purines, derived from dietary intake of purines (approximately 100 mg/d). Under normal conditions, the uric acid pool in the body amounts to 1200 mg, with about 700 mg of uric acid produced daily. Of this, ⅔ is excreted through the kidneys, ⅓ through the intestines, and a very small amount is excreted through the sweat glands. Therefore, the commonly used uric acid-lowering drugs in clinical practice include xanthine oxidase (XO) inhibitors (such as allopurinol and febuxostat) that suppress uric acid production, and Urat1 inhibitors that promote uric acid excretion (such as benzbromarone and lesinurad).

Xanthine oxidase is an enzyme with low specificity; it can catalyze the conversion from hypoxanthine into xanthine and subsequently into uric acid, as well as directly catalyze the conversion from xanthine to uric acid. Xanthine oxidase inhibitors are first-line options for treating hyperuricemia, with allopurinol and febuxostat being the primary marketed medications. However, such drugs do not meet the clinical needs of all patients and have noticeable side effects. Allopurinol is the only uric acid-lowering therapeutic agent available worldwide, but it can lead to serious adverse skin events. Severe hypersensitivity reactions related to allopurinol are closely associated with the human leukocyte antigen (HLA)-B*5801, with the Chinese population having a higher incidence of HLA-B*5801 positivity (6% to 8%) compared to Caucasians (about 2%), thus increasing the risk of hypersensitivity reactions. Febuxostat has a superior uric acid-lowering effect compared to allopurinol, but even at high doses of 80 mg per day, 40% to 52% of patients do not achieve the expected uric acid reduction target, and it may increase the incidence of acute gout attacks.

There is still an unmet clinical need in the market for safe and effective uric acid-lowering drugs.

Content of the Present Invention

The present disclosure provides a crystal form A of a compound of formula (I), wherein the crystal form A has an X-ray powder diffraction pattern comprising characteristic diffraction peaks at the following 2θ angles: 12.35±0.20°, 15.05±0.20°, 18.19±0.20°, 20.10±0.20°, 23.05±0.20°, 25.05±0.20°, 25.87±0.20°, and 27.16±0.20°, (I)

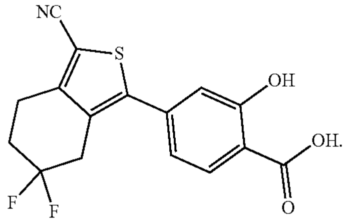

In some embodiments of the present disclosure, the X-ray powder diffraction pattern of the crystal form A has characteristic diffraction peaks at the following 2θ angles: 10.89±0.20°, 12.35±0.20°, 13.42±0.20°, 15.05±0.20°, 18.19±0.20°, 20.10±0.20°, 21.82±0.20°, 23.05±0.20°, 25.05±0.20°, 25.87±0.20°, 27.16±0.20°, and 30.28±0.20°.

In some embodiments of the present disclosure, the X-ray powder diffraction pattern of the crystal form A has characteristic diffraction peaks at the following 2θ angles: 6.72°, 8.94°, 10.89°, 12.35°, 13.42°, 15.05°, 17.26°, 18.19°, 18.70°, 20.10°, 21.82°, 23.05°, 24.28°, 25.05°, 25.87°, 27.16°, 29.41°, 30.28°, 30.89°, 33.58°, 36.29°, 37.29°, and 38.99°.

In some embodiments of the present disclosure, the crystal form A has an XRPD pattern basically as shown in FIG. 1.

In some embodiments of the present disclosure, the analysis data of the XRPD pattern of the crystal form A is as shown in Table 1:

TABLE 1

Analysis data of XRPD pattern for crystal form A

| No. | 2θ (°) | d-Spacing (Å) | Intensity (count) | Relative Intensity (%) |
|---|---|---|---|---|
| 1 | 6.72 | 13.15 | 280.7 | 7.8 |
| 2 | 8.94 | 9.88 | 169.3 | 2.5 |

TABLE 1-continued

Analysis data of XRPD pattern for crystal form A

| No. | 2θ (°) | d-Spacing (Å) | Intensity (count) | Relative Intensity (%) |
|---|---|---|---|---|
| 3 | 10.89 | 8.12 | 484.6 | 19.4 |
| 4 | 12.35 | 7.16 | 1328.1 | 65.1 |
| 5 | 13.42 | 6.59 | 558.1 | 22.7 |
| 6 | 15.05 | 5.88 | 938.4 | 43.7 |
| 7 | 17.26 | 5.13 | 332.4 | 9.2 |
| 8 | 18.19 | 4.87 | 761.9 | 31.6 |
| 9 | 18.70 | 4.74 | 360.9 | 8.9 |
| 10 | 20.10 | 4.41 | 738.3 | 27.6 |
| 11 | 21.82 | 4.07 | 563.7 | 15.5 |
| 12 | 23.05 | 3.85 | 2059.3 | 97.0 |
| 13 | 24.28 | 3.66 | 280.7 | 9.2 |
| 14 | 25.05 | 3.55 | 169.3 | 24.6 |
| 15 | 25.87 | 3.44 | 484.6 | 100.0 |
| 16 | 27.16 | 3.28 | 1328.1 | 33.7 |
| 17 | 29.41 | 3.03 | 558.1 | 7.8 |
| 18 | 30.28 | 2.95 | 938.4 | 23.0 |
| 19 | 30.89 | 2.89 | 332.4 | 12.8 |
| 20 | 33.58 | 2.67 | 761.9 | 6.6 |
| 21 | 36.29 | 2.47 | 360.9 | 3.0 |
| 22 | 37.29 | 2.41 | 738.3 | 4.6 |
| 23 | 38.99 | 2.31 | 563.7 | 6.3 |

In some embodiments of the present disclosure, the crystal form A has a thermogravimetric analysis curve with a weight loss of 1.96% at 200° C.±3° C.

In some embodiments of the present disclosure, the crystal form A has a TGA pattern as shown in FIG. 2.

In some embodiments of the present disclosure, the crystal form A has a differential scanning calorimetry curve comprising an endothermic peak with an onset at 244.3° C.±2° C.

In some embodiments of the present disclosure, the crystal form A has a DSC pattern as shown in FIG. 3.

The present disclosure provides a crystal form B of a compound of formula (I), wherein the crystal form A has an X-ray powder diffraction pattern comprising characteristic diffraction peaks at the following 2θ angles: 23.93±0.20°, 24.73±0.20°, and 26.58±0.20°,

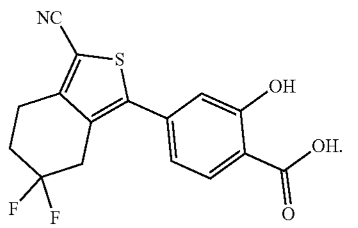

(I)

In some embodiments of the present disclosure, the X-ray powder diffraction pattern of the crystal form B has characteristic diffraction peaks at the following 2θ angles: 13.02±0.20°, 14.68±0.20°, 16.44±0.20°, 19.50±0.20°, 22.69±0.20°, 23.93±0.20°, 24.73±0.20°, and 26.58±0.20°.

In some embodiments of the present disclosure, the X-ray powder diffraction pattern of the crystal form B has characteristic diffraction peaks at the following 2θ angles: 13.02±0.20°, 14.68±0.20°, 16.44±0.20°, 19.50±0.20°, 22.69±0.20°, 23.93±0.20°, 24.73±0.20°, 25.87±0.20°, 26.58±0.20°, 28.98±0.20°, 29.34±0.20°, and 31.86±0.20°.

In some embodiments of the present disclosure, the X-ray powder diffraction pattern of the crystal form B has characteristic diffraction peaks at the following 2θ angles: 5.37°, 11.72°, 13.02°, 14.68°, 15.44°, 16.05°, 16.44°, 16.94°, 18.68°, 19.50°, 20.69°, 21.13°, 21.32°, 21.70°, 22.41°, 22.69°, 23.46°, 23.93°, 24.73°, 25.87°, 26.58°, 27.78°, 28.98°, 29.34°, 29.66°, 30.07°, 31.26°, 31.38°, 31.86°, 32.73°, 33.71°, 34.02°, 34.68°, 35.41°, 36.64°, 37.30°, 37.86°, and 38.30°.

In some embodiments of the present disclosure, the crystal form B has an XRPD pattern basically as shown in FIG. 4.

In some embodiments of the present disclosure, the analysis data of the XRPD pattern of the crystal form B is as shown in Table 2:

TABLE 2

Analysis data of XRPD pattern for crystal form B

| No. | 2θ (°) | d-Spacing (Å) | Intensity (count) | Relative intensity (%) |
|---|---|---|---|---|
| 1 | 5.37 | 16.44 | 173.7 | 3.9 |
| 2 | 11.72 | 7.54 | 170.2 | 4.1 |
| 3 | 13.02 | 6.79 | 862.1 | 27.1 |
| 4 | 14.68 | 6.03 | 466.2 | 13.4 |
| 5 | 15.44 | 5.73 | 228.2 | 5.2 |
| 6 | 16.05 | 5.52 | 158.1 | 2.7 |
| 7 | 16.44 | 5.39 | 521.0 | 14.9 |
| 8 | 16.94 | 5.23 | 248.3 | 5.7 |
| 9 | 18.68 | 4.75 | 125.0 | 1.8 |
| 10 | 19.50 | 4.55 | 563.4 | 16.3 |
| 11 | 20.69 | 4.29 | 183.5 | 3.2 |
| 12 | 21.13 | 4.20 | 176.1 | 2.8 |
| 13 | 21.32 | 4.17 | 186.3 | 3.1 |
| 14 | 21.70 | 4.09 | 166.2 | 2.3 |
| 15 | 22.41 | 3.96 | 469.6 | 12.2 |
| 16 | 22.69 | 3.92 | 652.7 | 18.2 |
| 17 | 23.46 | 3.79 | 275.0 | 4.9 |
| 18 | 23.93 | 3.72 | 1351.7 | 41.0 |
| 19 | 24.73 | 3.60 | 3109.3 | 100.0 |
| 20 | 25.87 | 3.44 | 346.8 | 6.7 |
| 21 | 26.58 | 3.35 | 1847.7 | 57.6 |
| 22 | 27.78 | 3.21 | 228.0 | 3.8 |
| 23 | 28.98 | 3.08 | 293.8 | 6.8 |
| 24 | 29.34 | 3.04 | 373.0 | 9.5 |
| 25 | 29.66 | 3.01 | 244.0 | 5.2 |
| 26 | 30.07 | 2.97 | 179.1 | 3.1 |
| 27 | 31.26 | 2.86 | 196.4 | 3.9 |
| 28 | 31.38 | 2.85 | 153.5 | 2.4 |
| 29 | 31.86 | 2.81 | 314.4 | 7.9 |
| 30 | 32.73 | 2.73 | 101.5 | 1.0 |
| 31 | 33.71 | 2.66 | 178.8 | 3.5 |
| 32 | 34.02 | 2.63 | 176.7 | 3.4 |
| 33 | 34.68 | 2.58 | 159.2 | 2.7 |
| 34 | 35.41 | 2.53 | 148.9 | 2.5 |
| 35 | 36.64 | 2.45 | 125.2 | 1.6 |
| 36 | 37.30 | 2.41 | 135.3 | 1.6 |
| 37 | 37.86 | 2.37 | 145.9 | 1.9 |
| 38 | 38.30 | 2.35 | 144.7 | 1.8 |

The present disclosure provides a crystal of a compound of formula (I), wherein the crystal has an X-ray powder diffraction pattern comprising characteristic diffraction peaks at the following 2θ angles: 13.28±0.30°, 15.34±0.30°, and 25.14±0.30°, (I)

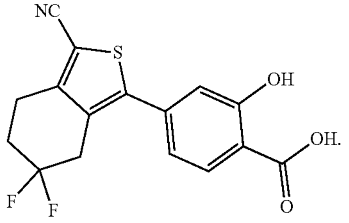

In some embodiments of the present disclosure, the X-ray powder diffraction pattern of the crystal has characteristic diffraction peaks at the following 2θ angles: 9.11±0.30°, 13.28±0.30°, 15.34±0.30°, 18.16±0.30°, 22.06±0.30°, 25.14±0.30°, 26.75±0.30°, and 27.25±0.30°.

In some embodiments of the present disclosure, the X-ray powder diffraction pattern of the crystal has characteristic diffraction peaks at the following 2θ angles: 9.11±0.30°, 11.21±0.30°, 13.28±0.30°, 15.34±0.30°, 18.16±0.30°, 22.06±0.30°, 23.15±0.30°, 25.14±0.30°, 25.97±0.30°, 26.75±0.30°, 27.25±0.30°, and 30.82±0.30°.

The present disclosure provides a crystal of a compound of formula (I), wherein the crystal has an X-ray powder diffraction pattern comprising characteristic diffraction peaks at the following 2θ angles: 13.20±0.20°, 15.26±0.20°, and 25.07±0.20°, (I)

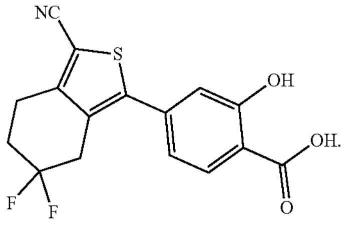

In some embodiments of the present disclosure, the X-ray powder diffraction pattern of the crystal has characteristic diffraction peaks at the following 2θ angles: 13.20±0.20°, 15.26±0.20°, 18.08±0.20°, 21.99±0.20°, 25.07±0.20°, 26.66±0.20°, 28.38±0.20°, and 30.70±0.20°.

In some embodiments of the present disclosure, the X-ray powder diffraction pattern of the crystal has characteristic diffraction peaks at the following 2θ angles: 9.03±0.20°, 11.13±0.20°, 13.20±0.20°, 15.26±0.20°, 18.08±0.20°, 21.99±0.20°, 25.07±0.20°, 26.66±0.20°, 28.38±0.20°, 29.41±0.20°, 30.70±0.20°, and 38.53±0.20°.

The present disclosure provides a crystal form C of a compound of formula (I), wherein the crystal form C has an X-ray powder diffraction pattern comprising characteristic diffraction peaks at the following 2θ angles: 13.20±0.20°, 18.08±0.20°, and 25.07±0.20°, (I)

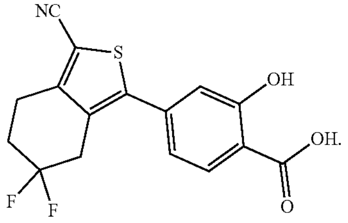

In some embodiments of the present disclosure, the X-ray powder diffraction pattern of the crystal form C has characteristic diffraction peaks at the following 2θ angles: 13.20±0.20°, 15.26±0.20°, 18.08±0.20°, 21.99±0.20°, 25.07±0.20°, 26.66±0.20°, 28.38±0.20°, and 30.70±0.20°.

In some embodiments of the present disclosure, the X-ray powder diffraction pattern of the crystal form C has characteristic diffraction peaks at the following 2θ angles: 13.20±0.20°, 15.26±0.20°, 18.08±0.20°, 21.99±0.20°, 25.07±0.20°, 25.38±0.20°, 26.66±0.20°, and 30.70±0.20°.

In some embodiments of the present disclosure, the X-ray powder diffraction pattern of the crystal form C has characteristic diffraction peaks at the following 2θ angles: 9.03±0.20°, 11.13±0.20°, 13.20±0.20°, 15.26±0.20°, 18.08±0.20°, 21.99±0.20°, 25.07±0.20°, 26.66±0.20°, 28.38±0.20°, 29.41±0.20°, 30.70±0.20°, and 38.53±0.20°.

In some embodiments of the present disclosure, the X-ray powder diffraction pattern of the crystal form C has characteristic diffraction peaks at the following 2θ angles: 9.03±0.20°, 13.20±0.20°, 15.26±0.20°, 18.08±0.20°, 21.99±0.20°, 25.07±0.20°, 25.38±0.20°, 26.66±0.20°, 28.38±0.20°, 29.41±0.20°, 30.70±0.20°, and 38.53±0.20°.

In some embodiments of the present disclosure, the X-ray powder diffraction pattern of the crystal form C has characteristic diffraction peaks at the following 2θ angles: 9.03±0.20°, 11.13±0.20°, 13.20±0.20°, 15.26±0.20°, 18.08±0.20°, 21.99±0.20°, 24.09±0.20°, 25.07±0.20°, 25.38±0.20°, 26.66±0.20°, 27.17±0.20°, 28.38±0.20°, 29.41±0.20°, 30.70±0.20°, 31.02±0.20°, and 38.53±0.20°.

In some embodiments of the present disclosure, the X-ray powder diffraction pattern of the crystal form C has characteristic diffraction peaks at the following 2θ angles: 13.20±0.20°, 25.07±0.20°, and alternatively at 18.08±0.20°, and/or 9.03±0.20°, and/or 11.13±0.20°, and/or 15.26±0.20°, and/or 18.92±0.20°, and/or 21.99±0.20°, and/or 24.09±0.20°, and/or 25.38±0.20°, and/or 26.66±0.20°, and/or 27.17±0.20°, and/or 28.38±0.20°, and/or 29.41±0.20°, and/or 30.70±0.20°, and/or 31.02±0.20°, and/or 33.67±0.20°, and/or 35.40±0.20°, and/or 36.35±0.20°, and/or 37.26±0.20°, and/or 38.53±0.20°.

In some embodiments of the present disclosure, the X-ray powder diffraction pattern of the crystal form C has characteristic diffraction peaks at the following 2θ angles: 9.03°, 11.13°, 13.20°, 15.26°, 18.08°, 18.92°, 21.99°, 24.09°, 25.07°, 25.38°, 26.66°, 27.17°, 28.38°, 29.41°, 30.70°, 31.02°, 33.67°, 35.40°, 36.35°, 37.26°, and 38.53°.

In some embodiments of the present disclosure, the X-ray powder diffraction pattern of the crystal form C has characteristic diffraction peaks at the following 2θ angles: 5.66°, 9.03°, 11.13°, 13.20°, 13.70°, 15.26°, 17.25°, 18.08°, 18.92°, 20.88°, 21.99°, 23.41°, 24.09°, 25.07°, 25.38°, 25.99°, 26.66°, 27.17°, 28.38°, 29.41°, 29.98°, 30.70°, 31.02°, 31.72°, 33.67°, 35.40°, 36.35°, 36.74°, 37.26°, 38.53°, and 39.80°.

In some embodiments of the present disclosure, the crystal form C has an XRPD pattern basically as shown in FIG. 5.

In some embodiments of the present disclosure, the analysis data of the XRPD pattern of the crystal form C is as shown in Table 3:

TABLE 3

Analysis data of XRPD pattern for crystal form C

| No. | 2θ (°) | d-Spacing (Å) | Intensity (count) | Relative intensity (%) |
|---|---|---|---|---|
| 1 | 5.66 | 15.61 | 81.3 | 0.4 |
| 2 | 9.03 | 9.78 | 486.5 | 7.6 |
| 3 | 11.13 | 7.95 | 389.0 | 5.9 |
| 4 | 13.20 | 6.70 | 2604.5 | 44.3 |
| 5 | 13.70 | 6.46 | 123.0 | 1.1 |
| 6 | 15.26 | 5.80 | 1579.6 | 26.4 |
| 7 | 17.25 | 5.14 | 94.0 | 0.6 |
| 8 | 18.08 | 4.90 | 732.1 | 11.6 |
| 9 | 18.92 | 4.69 | 188.7 | 2.3 |
| 10 | 20.88 | 4.25 | 152.3 | 1.6 |
| 11 | 21.99 | 4.04 | 1355.5 | 22.3 |
| 12 | 23.41 | 3.80 | 139.8 | 1.1 |
| 13 | 24.09 | 3.69 | 335.1 | 4.2 |
| 14 | 25.07 | 3.55 | 5882.0 | 100.0 |
| 15 | 25.38 | 3.51 | 811.7 | 11.9 |
| 16 | 25.99 | 3.43 | 191.5 | 1.0 |
| 17 | 26.66 | 3.34 | 766.1 | 11.0 |
| 18 | 27.17 | 3.28 | 465.7 | 5.9 |
| 19 | 28.38 | 3.14 | 596.2 | 8.5 |
| 20 | 29.41 | 3.04 | 461.3 | 6.4 |
| 21 | 29.98 | 2.98 | 182.7 | 1.7 |
| 22 | 30.70 | 2.91 | 610.0 | 9.2 |
| 23 | 31.02 | 2.88 | 293.9 | 3.7 |
| 24 | 31.72 | 2.82 | 130.9 | 1.0 |
| 25 | 33.67 | 2.66 | 201.6 | 2.3 |
| 26 | 35.40 | 2.53 | 194.3 | 2.1 |
| 27 | 36.35 | 2.47 | 194.0 | 2.1 |
| 28 | 36.74 | 2.44 | 103.0 | 0.4 |
| 29 | 37.26 | 2.41 | 289.4 | 3.6 |
| 30 | 38.53 | 2.33 | 491.1 | 7.1 |
| 31 | 39.80 | 2.26 | 116.0 | 0.6 |

In some embodiments of the present disclosure, the crystal form C has a thermogravimetric analysis curve with a weight loss of 1.21% at 200° C.±3° C.

In some embodiments of the present disclosure, the crystal form C has a TGA pattern as shown in FIG. 6.

In some embodiments of the present disclosure, the crystal form C has a differential scanning calorimetry curve comprising an endothermic peak with an onset at 250.0° C.±2° C.

In some embodiments of the present disclosure, the crystal form C has a DSC pattern as shown in FIG. 7.

The present disclosure provides a crystal form D of a compound of formula (I), wherein the crystal form D has an X-ray powder diffraction pattern comprising characteristic diffraction peaks at the following 2θ angles: 6.71±0.20°, 11.87±0.20°, and 25.21±0.20°,

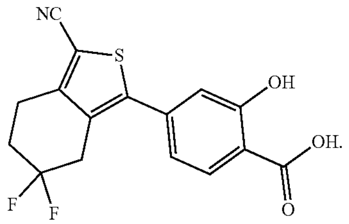

(I)

In some embodiments of the present disclosure, the X-ray powder diffraction pattern of the crystal form D has characteristic diffraction peaks at the following 2θ angles: 6.71±0.20°, 11.87±0.20°, 13.39±0.20°, 15.44±0.20°, 20.77±0.20°, 22.16±0.20°, 25.21±0.20°, and 27.05±0.20°.

In some embodiments of the present disclosure, the X-ray powder diffraction pattern of the crystal form D has characteristic diffraction peaks at the following 2θ angles: 6.71±0.20°, 11.87±0.20°, 13.39±0.20°, 15.44±0.20°, 16.32±0.20°, 17.90±0.20°, 20.77±0.20°, 22.16±0.20°, 24.31±0.20°, 25.21±0.20°, 27.05±0.20°, and 27.41±0.20°.

In some embodiments of the present disclosure, the X-ray powder diffraction pattern of the crystal form D has characteristic diffraction peaks at the following 2θ angles: 6.45°, 6.71°, 9.22°, 10.40°, 11.61°, 11.87°, 12.53°, 13.39°, 13.82°, 15.44°, 16.32°, 17.37°, 17.90°, 18.27°, 19.07°, 19.67°, 19.90°, 20.77°, 22.16°, 24.31°, 25.21°, 26.10°, 27.05°, 27.41°, 28.50°, 29.59°, 30.10°, 30.89°, 31.17°, 32.81°, 33.77°, 34.17°, 35.52°, 36.57°, 38.20°, and 38.68°.

In some embodiments of the present disclosure, the crystal form D has an XRPD pattern basically as shown in FIG. 8.

In some embodiments of the present disclosure, the analysis data of the XRPD pattern of the crystal form D is as shown in Table 4:

TABLE 4

Analysis data of XRPD pattern for crystal form D

| No. | 2θ (°) | d-Spacing (Å) | Intensity (count) | Relative intensity (%) |
|---|---|---|---|---|
| 1 | 6.45 | 13.69 | 388.2 | 19.2 |
| 2 | 6.71 | 13.16 | 808.2 | 43.1 |
| 3 | 9.22 | 9.59 | 183.7 | 7.6 |
| 4 | 10.40 | 8.50 | 146.8 | 4.9 |
| 5 | 11.61 | 7.62 | 911.3 | 47.2 |
| 6 | 11.87 | 7.45 | 1495.6 | 80.3 |
| 7 | 12.53 | 7.06 | 144.2 | 3.1 |
| 8 | 13.39 | 6.61 | 853.2 | 43.5 |
| 9 | 13.82 | 6.40 | 113.5 | 1.5 |
| 10 | 15.44 | 5.74 | 694.4 | 34.2 |
| 11 | 16.32 | 5.43 | 499.1 | 22.8 |
| 12 | 17.37 | 5.10 | 249.1 | 7.9 |
| 13 | 17.90 | 4.95 | 607.5 | 27.8 |
| 14 | 18.27 | 4.85 | 385.7 | 14.9 |
| 15 | 19.07 | 4.65 | 348.7 | 12.4 |
| 16 | 19.67 | 4.51 | 324.5 | 11.0 |
| 17 | 19.90 | 4.46 | 269.9 | 7.9 |
| 18 | 20.77 | 4.27 | 735.7 | 34.6 |
| 19 | 22.16 | 4.01 | 905.2 | 43.7 |
| 20 | 24.31 | 3.66 | 766.1 | 33.7 |
| 21 | 25.21 | 3.53 | 1945.9 | 100.0 |
| 22 | 26.10 | 3.41 | 433.2 | 13.5 |
| 23 | 27.05 | 3.29 | 1193.7 | 56.7 |
| 24 | 27.41 | 3.25 | 545.7 | 20.0 |
| 25 | 28.50 | 3.13 | 313.9 | 7.3 |
| 26 | 29.59 | 3.02 | 383.0 | 11.9 |
| 27 | 30.10 | 2.97 | 311.3 | 8.1 |

TABLE 4-continued

| Analysis data of XRPD pattern for crystal form D | | | | |
|---|---|---|---|---|
| No. | 2θ (°) | d-Spacing (Å) | Intensity (count) | Relative intensity (%) |
| 28 | 30.89 | 2.89 | 351.2 | 11.1 |
| 29 | 31.17 | 2.87 | 255.8 | 5.9 |
| 30 | 32.81 | 2.73 | 234.1 | 6.6 |
| 31 | 33.77 | 2.65 | 187.9 | 4.2 |
| 32 | 34.17 | 2.62 | 153.8 | 2.6 |
| 33 | 35.52 | 2.53 | 163.2 | 3.1 |
| 34 | 36.57 | 2.46 | 157.2 | 2.3 |
| 35 | 38.20 | 2.35 | 234.0 | 6.6 |
| 36 | 38.68 | 2.33 | 269.2 | 8.9 |

In some embodiments of the present disclosure, the crystal form D has a thermogravimetric analysis curve with a weight loss of 1.14% at 200° C.±3° C.

In some embodiments of the present disclosure, the crystal form D has a TGA pattern as shown in FIG. 9.

In some embodiments of the present disclosure, the crystal form D has a differential scanning calorimetry curve comprising an endothermic peak with an onset at 251.4° C.±2° C.

In some embodiments of the present disclosure, the crystal form D has a DSC pattern as shown in FIG. 10.

The present disclosure provides a crystal form E of a compound of formula (I), wherein the crystal form E has an X-ray powder diffraction pattern comprising characteristic diffraction peaks at the following 2θ angles: 13.28±0.20°, 15.34±0.20°, and 25.14±0.20°, (I)

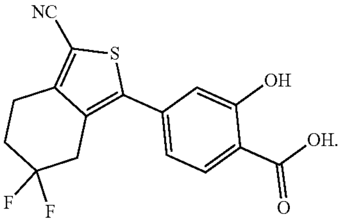

In some embodiments of the present disclosure, the X-ray powder diffraction pattern of the crystal form E has characteristic diffraction peaks at the following 2θ angles: 9.11±0.20°, 13.28±0.20°, 15.34±0.20°, 18.16±0.20°, 22.06±0.20°, 25.14±0.20°, 26.75±0.20°, and 27.25±0.20°.

In some embodiments of the present disclosure, the X-ray powder diffraction pattern of the crystal form E has characteristic diffraction peaks at the following 2θ angles: 9.11±0.20°, 12.43±0.20°, 13.28±0.20°, 15.34±0.20°, 18.16±0.20°, 22.06±0.20°, 23.15±0.20°, and 25.14±0.20°.

In some embodiments of the present disclosure, the X-ray powder diffraction pattern of the crystal form E has characteristic diffraction peaks at the following 2θ angles: 9.11±0.20°, 11.21±0.20°, 13.28±0.20°, 15.34±0.20°, 18.16±0.20°, 22.06±0.20°, 23.15±0.20°, 25.14±0.20°, 25.97±0.20°, 26.75±0.20°, 27.25±0.20°, and 30.82±0.20°.

In some embodiments of the present disclosure, the X-ray powder diffraction pattern of the crystal form E has characteristic diffraction peaks at the following 2θ angles: 9.11±0.20°, 11.21±0.20°, 12.43±0.20°, 13.28±0.20°, 15.34±0.20°, 18.16±0.20°, 22.06±0.20°, 23.15±0.20°, 25.14±0.20°, 25.97±0.20°, 26.75±0.20°, and 27.25±0.20°.

In some embodiments of the present disclosure, the X-ray powder diffraction pattern of the crystal form E has characteristic diffraction peaks at the following 2θ angles: 13.28±0.20°, 25.14±0.20°, and alternatively at 15.34±0.20°, and/or 9.11±0.20°, and/or 10.94±0.20°, and/or 11.21±0.20°, and/or 12.43±0.20°, and/or 18.16±0.20°, and/or 22.06±0.20°, and/or 23.15±0.20°, and/or 23.35±0.20°, and/or 24.19±0.20°, and/or 25.97±0.20°, and/or 26.75±0.20°, and/or 27.25±0.20°, and/or 28.45±0.20°, and/or 29.49±0.20°, and/or 30.82±0.20°, and/or 33.74±0.20°, and/or 36.39±0.20°, and/or 37.34±0.20°, and/or 38.57±0.20°.

In some embodiments of the present disclosure, the X-ray powder diffraction pattern of the crystal form E has characteristic diffraction peaks at the following 2θ angles: 9.11±0.20°, 10.94±0.20°, 11.21±0.20°, 12.43±0.20°, 13.28±0.20°, 15.34±0.20°, 18.16±0.20°, 22.06±0.20°, 23.15±0.20°, 23.35±0.20°, 24.19±0.20°, 25.14±0.20°, 25.97±0.20°, 26.75±0.20°, 27.25±0.20°, 28.45±0.20°, 29.49±0.20°, 30.82±0.20°, 33.74±0.20°, 36.39±0.20°, 37.34±0.20°, and 38.57±0.20°.

In some embodiments of the present disclosure, the X-ray powder diffraction pattern of the crystal form E has characteristic diffraction peaks at the following 2θ angles: 9.11°, 10.94°, 11.21°, 12.43°, 13.28°, 15.34°, 17.39°, 18.16°, 20.18°, 18.94°, 20.95°, 22.06°, 23.15°, 23.35°, 24.19°, 25.14°, 25.97°, 26.75°, 27.25°, 28.45°, 29.49°, 30.16°, 30.82°, 33.74°, 35.45°, 36.39°, 37.34°, and 38.57°.

In some embodiments of the present disclosure, the crystal form E has an XRPD pattern basically as shown in FIG. 11.

In some embodiments of the present disclosure, the analysis data of the XRPD pattern of the crystal form E is as shown in Table 5:

TABLE 5

| Analysis data of XRPD pattern for crystal form E | | | | |
|---|---|---|---|---|
| No. | 2θ (°) | d-Spacing (Å) | Intensity (count) | Relative intensity (%) |
| 1 | 9.11 | 9.70 | 338.4 | 12.3 |
| 2 | 10.94 | 8.08 | 148.7 | 4.2 |
| 3 | 11.21 | 7.89 | 252.2 | 8.4 |
| 4 | 12.43 | 7.12 | 212.8 | 6.4 |
| 5 | 13.28 | 6.66 | 1596.2 | 64.7 |
| 6 | 15.34 | 5.77 | 980.0 | 38.7 |
| 7 | 17.39 | 5.09 | 106.7 | 1.8 |
| 8 | 18.16 | 4.88 | 533.0 | 19.5 |
| 9 | 18.94 | 4.68 | 119.5 | 2.0 |
| 10 | 20.18 | 4.40 | 106.0 | 1.1 |
| 11 | 20.95 | 4.24 | 116.7 | 1.3 |
| 12 | 22.06 | 4.03 | 679.8 | 24.6 |
| 13 | 23.15 | 3.84 | 280.6 | 7.5 |
| 14 | 23.35 | 3.81 | 182.8 | 3.4 |
| 15 | 24.19 | 3.68 | 282.3 | 7.1 |
| 16 | 25.14 | 3.54 | 2494.0 | 100.0 |
| 17 | 25.97 | 3.43 | 322.3 | 7.8 |
| 18 | 26.75 | 3.33 | 393.5 | 10.8 |
| 19 | 27.25 | 3.27 | 389.2 | 10.8 |
| 20 | 28.45 | 3.13 | 255.5 | 5.6 |
| 21 | 29.49 | 3.03 | 242.9 | 5.4 |
| 22 | 30.16 | 2.96 | 157.5 | 2.0 |
| 23 | 30.82 | 2.90 | 341.7 | 10.2 |
| 24 | 33.74 | 2.65 | 160.5 | 3.6 |
| 25 | 35.45 | 2.53 | 148.1 | 2.9 |
| 26 | 36.39 | 2.47 | 161.8 | 3.3 |
| 27 | 37.34 | 2.41 | 169.5 | 3.3 |
| 28 | 38.57 | 2.33 | 261.0 | 7.3 |

In some embodiments of the present disclosure, the crystal form E has a thermogravimetric analysis curve with a weight loss of 0.79% at 200° C.±3° C.

In some embodiments of the present disclosure, the crystal form E has a TGA pattern as shown in FIG. 12.

In some embodiments of the present disclosure, the crystal form E has a differential scanning calorimetry curve comprising an endothermic peak with an onset at 250.4° C.±2° C.

In some embodiments of the present disclosure, the crystal form E has a DSC pattern as shown in FIG. 13.

The present disclosure also provides a use of the crystal forms A, B, C, D, and E of the compound of formula (I) in the manufacture of a medicament for treating gout and hyperuricemia.

Technical Effect

The compound of formula (I) has stable crystal properties and no hygroscopicity, showing good prospects for pharmaceutical development.

Definition and Description

Unless otherwise specified, the following terms and phrases used herein have the following meanings. A specific phrase or term should not be considered indefinite or unclear in the absence of a particular definition, but should be understood in the ordinary sense. When a trade name appears herein, it is intended to refer to its corresponding commodity or active ingredient thereof.

The intermediate compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred embodiments include but are not limited to the examples of the present disclosure.

The chemical reactions of the specific embodiments of the present disclosure are completed in a suitable solvent, and the solvent must be appropriate for the chemical changes of the present disclosure and the required reagents and materials thereof. To obtain the compounds of the present disclosure, sometimes it is necessary for those skilled in the art to modify or select synthetic processes or reaction schemes based on existing embodiments.

The present disclosure is described in detail by the examples below, but the examples don't constitute any restriction on the present disclosure.

All solvents used in the present disclosure are commercially available and require no further purification before use.

The compounds of the present disclosure are named according to the conventional naming principles in the art or by ChemDraw® software, and the commercially available compounds use the supplier catalog names.

The structure of the compounds of the present disclosure can be confirmed by conventional methods known to those skilled in the art, and if the present disclosure involves an absolute configuration of a compound, then the absolute configuration can be confirmed using conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: ϕ/ω scan, and after collecting the relevant data, the crystal structure can be further analyzed by direct method (Shelxs97).

The solvents used in the present disclosure are commercially available. The present disclosure uses the following abbreviations:—OMOM stands for methoxymethyl ether group; HPE stands for 100% inhibition rate activity; ZPE stands for 0% inhibition rate activity; DPBS stands for Dulbecco's Phosphate Buffered Saline.

X-ray powder diffractometer (XRPD) in the present disclosure

Instrument model: Bruker D2 PHASER X-ray diffractometer

Detailed parameters for XRPD are as follows:

Radiation source: Cu, k-Alphal (λ=1.54184 Å)

Tube voltage: 30 kV

Tube current: 10 mA

Divergence slit: 0.6 mm

Soller slits in the primary optics: 2.5°

Soller slits in the secondary optics: 2.5°

Detector slit: 5.827°

Antiscattering slit: 0 mm

Scan axis: θs-θd

Step size: 0.02 deg

Time per step: 0.2 seconds

Scanning Scope: 3-40 deg

Differential Scanning Calorimeter (DSC) in the Present Disclosure

Instrument model: TA Q2000 differential scanning calorimeter

Test method: A sample (about 1 mg) is taken and placed in a DSC aluminum pot for testing. Under the condition of 50 mL/min $N_2$, the sample is heated from 30° C. (room temperature) to 250° C. at a rate of 10° C./min.

Thermal Gravimetric Analyzer (TGA) in the Present Disclosure

Instrument model: DISCOVERY 5500 thermal gravimetric analyzer

Test method: A sample (2 to 5 mg) is taken and placed in a TGA platinum pot for testing. Under the condition of 25 mL/min $N_2$, the sample is heated from room temperature to 300° C. at a rate of 10° C./min.

Dynamic Vapor Sorption (DVS) in the Present Disclosure

Instrument model: Intrinsic dynamic vapor sorption analyzer Test conditions: A sample (10 to 30 mg) is taken and placed in a DVS sample tray for testing.

Detailed parameters for DVS are as follows:

Temperature: 25° C.

Equilibrium: dm/dt=0.002%/min (minimum: 10 minutes, maximum: 180 minutes)

RH (%) test increment: 10(90 to 0 to 90%), 5(90 to 95%)

RH (%) test increment range: 0% to 95% to 0%

The evaluation and classifications of hygroscopicity are shown in Table 6:

TABLE 6

Evaluation and classifications of hygroscopicity

| Classifications of hygroscopicity | ΔW % |
|---|---|
| Deliquescence | sufficient moisture is absorbed to produce a fluid |
| Highly hygroscopic | ΔW % ≥ 15% |
| Hygroscopic | 15% > ΔW % ≥ 2% |
| Slightly hygroscopic | 2% > ΔW % ≥ 0.2% |
| Non-hygroscopic or virtually non-hygroscopic | ΔW % < 0.2% |

Note:
ΔW % indicates weight increase of the sample via moisture absorption at 25 ± 1° C. and 80 ± 2% RH.

DETAILED DESCRIPTION OF THE PREFERRED EMBODIMENT

Figure 1:
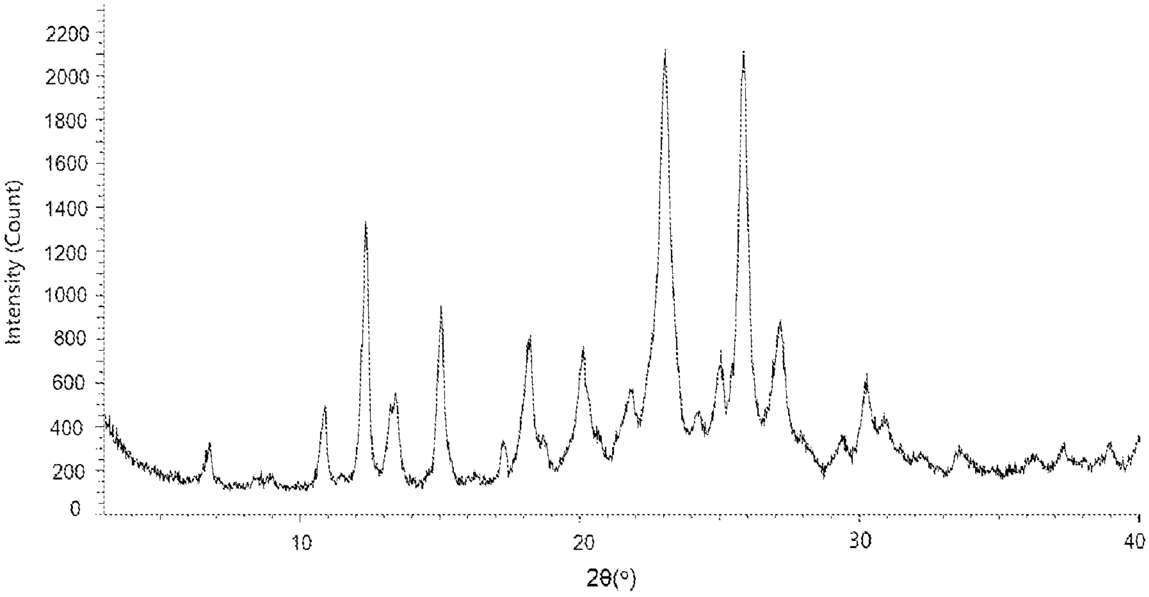
FIG. 1 is a Cu-Kα radiation XRPD pattern of the crystal form A of the compound of formula (I).

The present disclosure is described in detail by the examples below, but it does not mean that there are any adverse restrictions on the present disclosure. The present disclosure has been described in detail herein, and specific embodiments thereof have also been disclosed; for those skilled in the art, it is obvious to make various modifications and improvements to the embodiments of the present disclosure without departing from the spirit and scope of the present disclosure.

Example 1: Preparation of Crystal Form a of Compound of Formula (I)

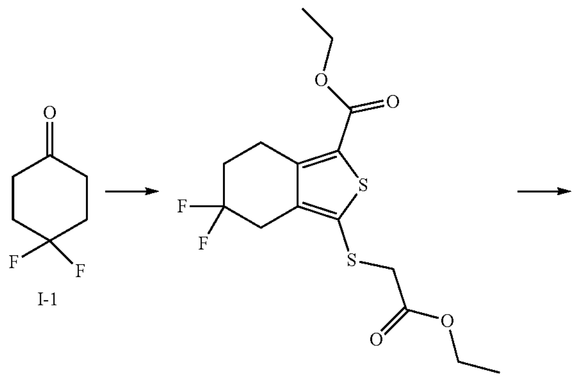

I-1

I-2

-continued

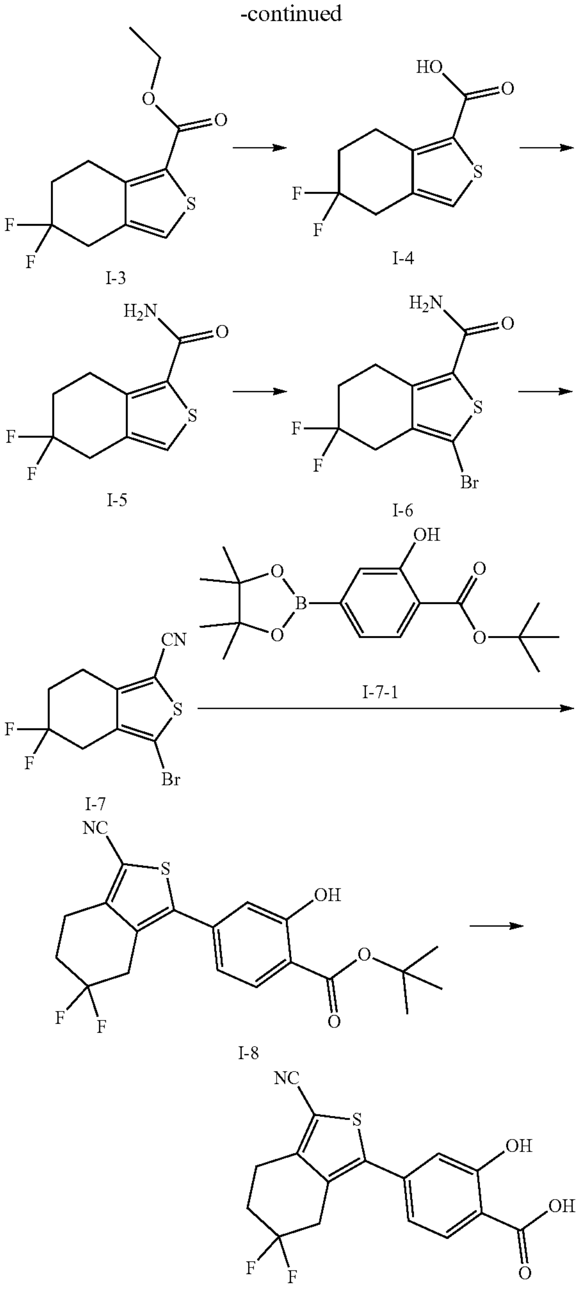

I-3

I-4

I-5

I-6

I-7-1

I-7

I-8

(I)

Step 1: Synthesis of Compound I-2

To dimethyl sulfoxide (1200 mL) was added potassium tert-butoxide (234.26 g, 2.09 mol). The mixture was stirred at room temperature till it was clear. A solution of compound I-1 (200 g, 1.49 mol) in dimethyl sulfoxide (500 mL) was dropwise added thereto at 15-20° C. After the addition, the mixture was stirred for another 40 minutes. Subsequently, carbon disulfide (113.54 g, 1.49 mol, 90.11 mL) was dropwise added thereto, and the reaction mixture was maintained at no higher than 20° C. After the addition, the mixture was stirred for another 20 minutes. The mixture was slowly added with potassium tert-butoxide (100.40 g, 894.70 mmol), maintained at between 15 and 20° C., and stirred for 30 minutes. Then ethyl bromoacetate (498.05 g, 2.98 mol, 329.83 mL) was dropwise added thereto. The mixture was maintained at between 15 and 20° C., and stirred for 1.5 hours at the same temperature. Potassium carbonate (206.09 g, 1.49 mol) was added thereto, and the reaction mixture was heated to 60° C., and stirred for another 1.5 hours. The reaction mixture was added with 1 L of water, added with 6 M hydrochloric acid aqueous solution to adjust the pH to between 3 and 4, and extracted with ethyl acetate (1.5 L×2). The combined organic phases were washed with saturated brine (200 mL×3), and dried under reduced pressure to remove the organic solvent. The resulting crude product was added with isopropanol (200 mL), stirred until uniform, left to stand for 15 hours, filtered, and dried under vacuum at 45° C. for 1 hour to obtain compound I-2. $^1$H NMR (400 MHZ, $CDCl_3$) δ: 4.32 (q, J=7.2 Hz, 2H), 4.19 (q, J=7.2 Hz, 2H), 3.56 (s, 2H), 3.25 (t, J=6.8 Hz, 2H), 3.19 (t, J=14.4 Hz, 2H), 2.26-2.17 (m, 2H), 1.37 (t, J=7.2 Hz, 3H), 1.27 (t, J=7.2 Hz, 3H). MS m/z=364.8 $[M+H]^+$.

Step 2: Synthesis of Compound I-3

Compound I-2 (282 g, 773.82 mmol) was dissolved in ethanol (3.5 L), and added with raney nickel (99.45 g, 1.16 mol). The reaction system was replaced with nitrogen three times, and stirred and reacted at 85° C. for 48 hours under a hydrogen pressure of 2.5 MPA. The reaction mixture was then cooled, and filtered through diatomite under nitrogen atmosphere. The filtrate was dried under reduced pressure to remove the solvent and compound I-3 was obtained. The resulting compound was directly used in the next step without further purification. $^1$H NMR (400 MHZ, $CDCl_3$) δ: 7.09 (s, 1H), 4.26 (q, J=7.2 Hz, 2H), 3.20 (t, J=6.8 Hz, 2H), 3.12 (t, J=14.4 Hz, 2H), 2.20-2.10 (m, 2H), 1.30 (t, J=6.8 Hz, 3H). MS m/z=247.0 $[M+H]^+$.

Step 3: Synthesis of Compound I-4

Compound I-3 (40.00 g, 162.42 mmol) was dissolved in methanol (200 mL). 200 mL of sodium hydroxide (12.99 g, 324.84 mmol) aqueous solution was added thereto, and the reaction mixture was heated to 50° C., and stirred for 2 hours. The reaction mixture was dried under reduced pressure to remove the organic solvent. The residue was added with 150 mL of water, and added with 6 M hydrochloric acid aqueous solution to adjust the pH to between 2 and 3, resulting in the precipitation of a large amount of white solid. The mixture was filtered. The filter cake was washed with 100 ml of water and 50 mL of petroleum ether, and dried under reduced pressure at 50° C. for 3 hours to obtain compound I-4. $^1$H NMR (400 MHZ, $CD_3OD$) δ: 7.38 (s, 1H), 3.33-3.17 (m, 4H), 2.28-2.21 (m, 2H).

Step 4: Synthesis of Compound I-5

Compound I-4 (35.0 g, 160.39 mmol) was dissolved in tetrahydrofuran (200 mL). Carbonyldiimidazole (33.81 g, 208.51 mmol) was added thereto. The reaction mixture was stirred for 2 hours under nitrogen atmosphere, then added with ammonia water (31.23 g, 240.58 mmol, 34.32 mL), and stirred for another 15 hours. The mixture was dried under reduced pressure to remove the organic solvent. The resulting residue was added with 300 mL of water, stirred for 10 minutes, and filtered. The filter cake was washed with 100 ml of water, dried under reduced pressure at 55° C. for 2.5 hours to obtain compound I-5. $^1$H NMR (400 MHZ, $CDCl_3$) δ: 7.09 (s, 1H), 5.72 (brs, 2H), 3.30-3.18 (m, 4H), 2.29-2.19 (m, 2H).

Step 5: Synthesis of Compound I-6

Compound I-5 (31 g, 142.70 mmol) was dissolved in N,N-dimethylformamide (200 mL). N-Bromosuccinimide (27.94 g, 156.97 mmol) was slowly added thereto in batches. The reaction mixture was stirred at 20° C. for another 2 hours. The reaction mixture was slowly poured into 600 mL of stirred water, resulting in the precipitation of a large amount of solid. After stirring for 10 minutes, the mixture was filtered. The filter cake was washed with 200 ml of water and 100 mL of petroleum ether, then dried under vacuum at 50° C. for 2 hours to obtain compound I-6. $^1$H NMR (400 MHZ, $CDCl_3$) δ: 5.62 (brs, 2H), 3.25 (t, J=7.2 Hz, 2H), 3.04 (t, J=14.0 Hz, 2H), 2.26-2.18 (m, 2H).

Step 6: Synthesis of Compound I-7

To ethyl acetate (250 mL) were added compound I-6 (48 g, 162.09 mmol) and triethylamine (32.80 g, 324.18 mmol, 45.12 mL). The mixture was cooled to 0° C. under nitrogen atmosphere, and then trifluoroacetic anhydride (44.26 g, 210.72 mmol, 29.31 mL) was dropwise added thereto. The reaction mixture was stirred for 1 hour at the same temperature, then warmed to 20° C., and stirred for another 0.5 hours. The reaction mixture was diluted with 250 mL of ethyl acetate, sequentially washed with water (100 mL×2), saturated sodium bicarbonate solution (150 mL), and saturated brine (100 mL), dried over anhydrous sodium sulfate, filtered, and dried under reduced pressure to remove the organic solvent. Thus compound I-7 was obtained, which was directly used in the next step without further purification. $^1$H NMR (400 MHZ, $CDCl_3$) δ: 3.13-2.97 (m, 4H), 2.30-2.20 (m, 2H).

Step 7: Synthesis of Compound I-8

To dimethoxyethane (60 mL) and water (12 mL) were added compound I-7 (6.0 g, 21.57 mmol), compound I-7-1 (7.60 g, 23.73 mmol), and anhydrous potassium phosphate (9.16 g, 43.15 mmol). Under nitrogen atmosphere, Pd(dppf)$Cl_2$ (394.64 mg, 539.34 μmol) was added thereto. The reaction mixture was heated to 85° C. under nitrogen atmosphere and stirred for another 15 hours. The reaction mixture was cooled, added with 20 ml of water and 100 mL of ethyl acetate, stirred for 10 minutes, and filtered. The organic phase was separated from the filtrate. The aqueous phase was extracted with ethyl acetate (30 mL×3). The combined organic phases were washed with saturated brine (30 mL), dried over anhydrous sodium sulfate, filtered, and dried under reduced pressure to remove the organic solvent. The resulting crude product was added with ethyl acetate (80 mL), and sequentially added with activated carbon (4 g) and silicon dioxide (4 g). The mixture was heated to 80° C., stirred for 1 hour, then cooled, filtered through diatomite, and dried under reduced pressure to remove the organic solvent. The resulting crude product was subsequently slurried with tert-butyl methyl ether (25 mL) at 25° C. for 0.5 hours, and filtered, and the resulting filter cake was dried under vacuum at 45° C. for 1 hour to obtain compound I-8. $^1$H NMR (400 MHZ, $CDCl_3$) δ: 11.18 (s, 1H), 7.86 (d, J=8.0 Hz, 1H), 7.01 (d, J=1.6 Hz, 1H), 6.92-6.90 (m, 1H), 3.24 (t, J=14.4 Hz, 2H), 3.12 (t, J=6.8 Hz, 2H), 2.36-2.26 (m, 2H), 1.64 (s, 9H).

Step 8: Synthesis of Crystal Form a of Compound of Formula (I)

Figure 2:
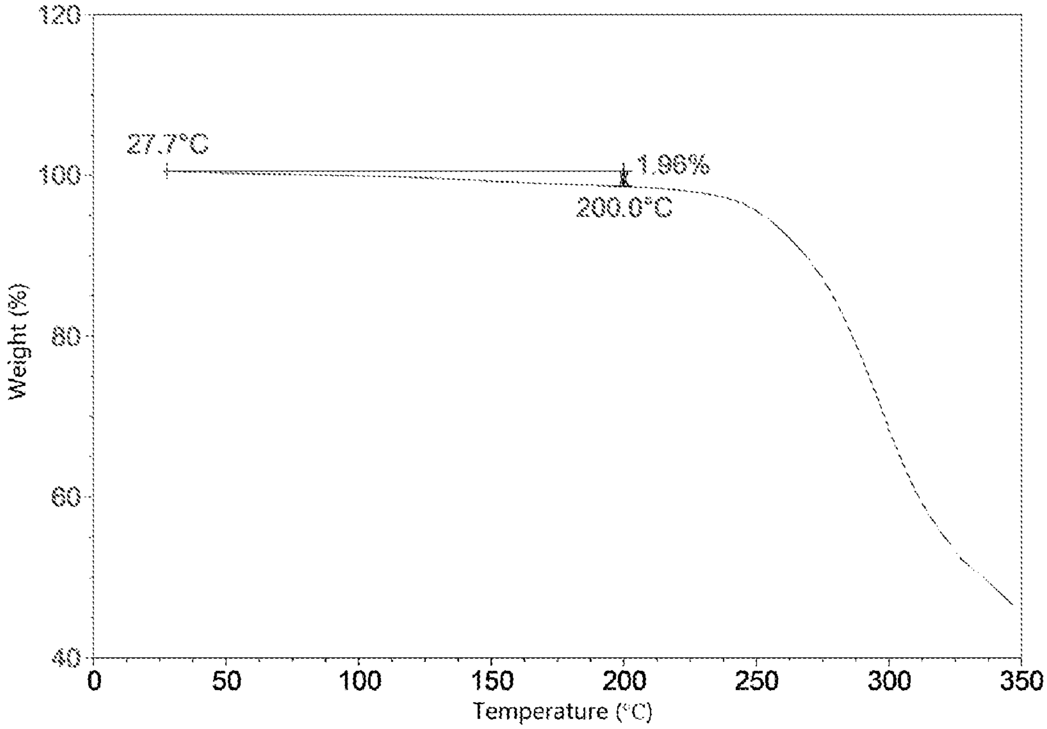
FIG. 2 is a TGA pattern of the crystal form A of the compound of formula (I).
Figure 3:
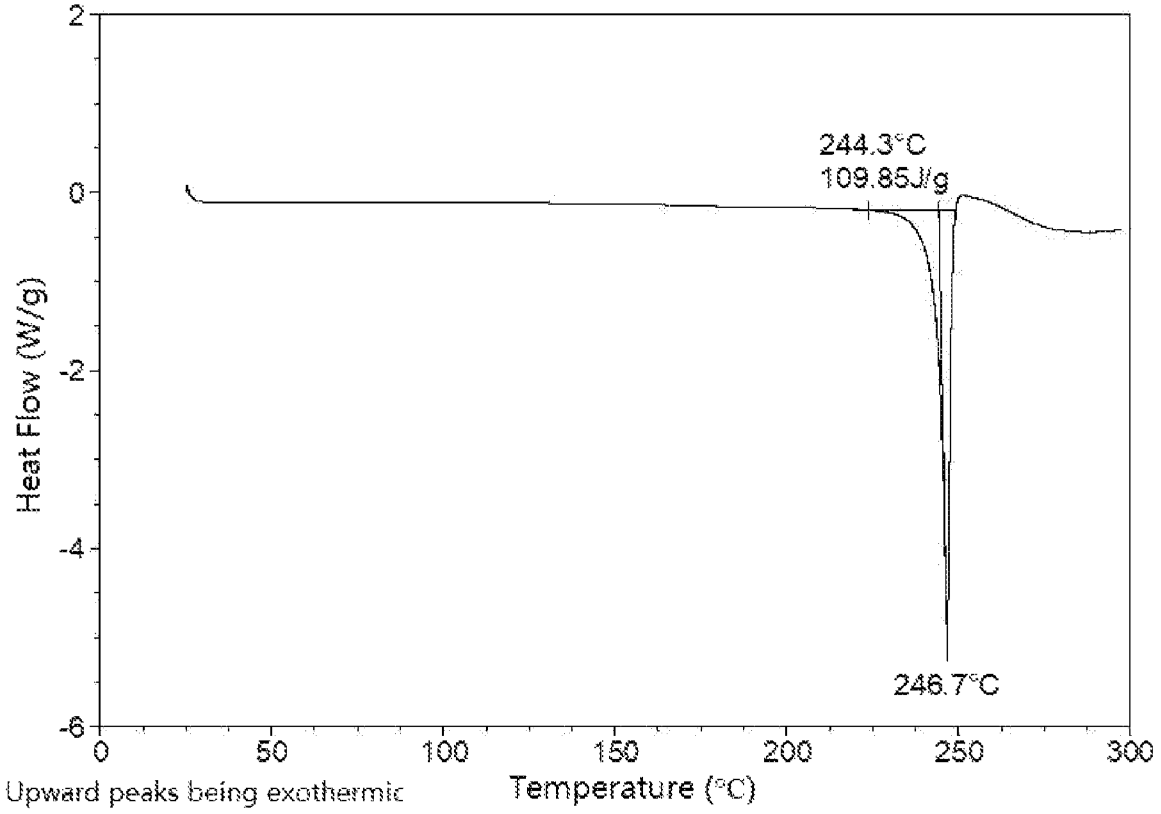
FIG. 3 is a DSC pattern of the crystal form A of the compound of formula (I).

Compound I-8 (32 g, 81.75 mmol) was added to trifluoroacetic acid (250 mL), and the reaction mixture was stirred at 20° C. for 1 hour. The trifluoroacetic acid was removed under reduced pressure, and water (300 mL) was added to the resulting residue. The mixture was slurried at room temperature for 20 minutes until completely dispersed, and filtered. The filter cake was washed with water (200 mL), and dried under reduced pressure at 45° C. for 1 hour to obtain the crystal form A of the compound of formula (I). $^1$H NMR (400 MHZ, $CD_3OD$) δ: 8.03-7.96 (m, 1H), 7.12-7.06 (m, 2H), 3.36-3.29 (m, 2H), 3.16-3.07 (m, 2H), 2.44-2.30 (m, 2H). The XRPD pattern of crystal form A is shown in FIG. 1, the TGA pattern thereof is shown in FIG. 2, and the DSC pattern thereof is shown in FIG. 3.

Example 2: Preparation of Compound of Formula (I)

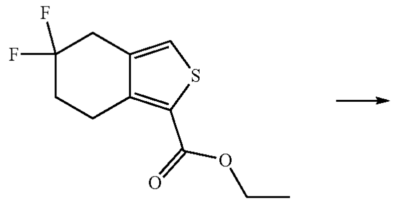

I-3

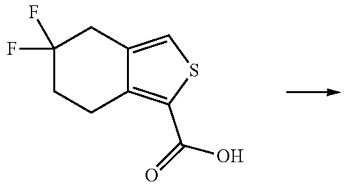

I-4

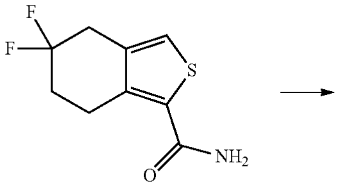

I-5

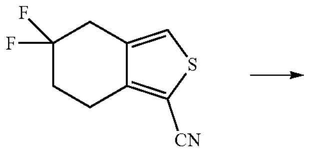

2-4

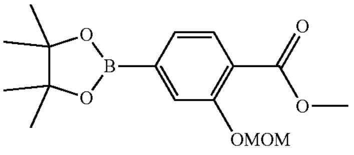

2-5A

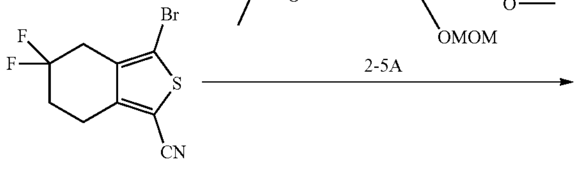

I-7

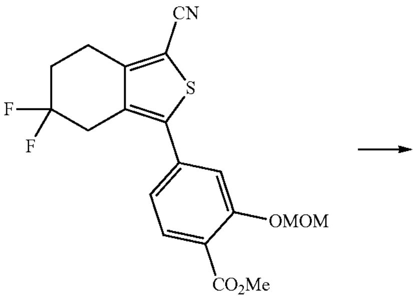

2-6

-continued

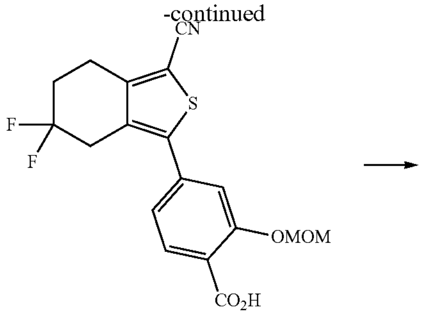

2-7

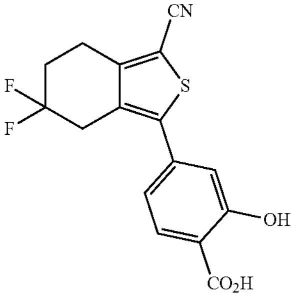

(I)

Step 1: Synthesis of Compound I-4

Compound I-3 (2.5 g, 10.15 mmol) was dissolved in methanol (10 mL), and then water (10 mL) and sodium hydroxide (1.62 g, 40.61 mmol) were added thereto. The resulting reaction mixture was placed in an oil bath at 40° C. and stirred for 2 hours. The reaction mixture was then reduced to half under reduced pressure, and water (5 mL) was added to the residue. Upon stirring, the mixture was added with 6 M hydrochloric acid to adjust the pH to between 2 and 3, resulting in the precipitation of a large amount of white solid. The solid was collected through filtration, and dried under reduced pressure at 50° C. for 3 hours to obtain compound I-4. $^1$H NMR (400 MHZ, $CDCl_3$) δ: 7.28 (s, 1H), 3.30 (t, J=7.0 Hz, 2H), 3.22 (t, J=14.3 Hz, 2H), 2.25 (tt, J=6.8, 13.4 Hz, 2H).

Step 2: Synthesis of Compound I-5

Compound I-4 (500 mg, 2.29 mmol) was dissolved in dichloromethane (5 mL), and then carbonyldiimidazole (445.83 mg, 2.75 mmol) was added thereto. The resulting reaction mixture was stirred, reacted for 1 hour under nitrogen atmosphere, and poured into a vigorously stirred ammonia water (2.87 g, 22.91 mmol, 3.15 mL, content of 28%) in tetrahydrofuran (5 mL). The reaction mixture was stirred and reacted for 30 minutes. The reaction mixture was concentrated under reduced pressure at 25° C. The residue was extracted with ethyl acetate (20 mL×3). The organic phases were combined, and then dried by rotary evaporation to give a crude product. The crude product was purified by column chromatography (ethyl acetate/petroleum ether=0 to 45%) to obtain compound I-5. $^1$H NMR (400 MHZ, $CDCl_3$) δ: 7.10 (s, 1H), 5.58 (br s, 2H), 3.28 (t, J=6.9 Hz, 2H), 3.21 (t, J=14.4 Hz, 2H), 2.24 (tt, J=6.9, 13.4 Hz, 2H).

Step 3: Synthesis of Compound 2-4

Compound I-5 (320 mg, 1.47 mmol) was dissolved in DMF (3 mL), and the resulting solution was cooled to 0° C., and then cyanuric chloride (298.81 mg, 1.62 mmol) was added thereto. The final reaction mixture was stirred for 2 hours under nitrogen atmosphere (during which a large amount of white solid precipitated). The reaction mixture was diluted with ethyl acetate (50 mL), and then washed with water (10 mL×3) and saturated brine (10 mL). The organic phase was dried over an appropriate amount of anhydrous sodium sulfate, and filtered to remove any drying agent. The reaction mixture was concentrated under reduced pressure to remove the solvent and obtain the crude product 2-4, which was directly used in the next step. $^1$H NMR: (400 MHZ, $CDCl_3$) δ: 7.25 (s, 1H), 3.21 (t, J=14.3 Hz, 2H), 3.09 (t, J=6.9 Hz, 2H), 2.28 (tt, J=6.8, 13.2 Hz, 2H).

Step 4: Synthesis of Compound 2-5

Compound 2-4 (290 mg, 1.46 mmol) was dissolved in acetic acid (2 mL), and then liquid bromine (348.94 mg, 2.18 mmol, 112.56 μL) was added thereto. The resulting reaction mixture was stirred at 25° C. (room temperature) for 15 hours. The reaction mixture was then dried by rotary evaporation, and ethyl acetate (30 mL) was added to the residue. The mixture was added with saturated sodium carbonate aqueous solution to adjust the pH to between 7 and 8, and the organic phase was separated. The aqueous phase was extracted with ethyl acetate (30 mL). The organic phases were combined and concentrated under reduced pressure to obtain a crude product. The crude product was purified by column chromatography (ethyl acetate/petroleum ether=0 to 5%) to obtain compound I-7. $^1$H NMR: (400 MHZ, $CDCL_3$) δ: 3.10-2.99 m, 4H), 2.32-2.19 (m, 2H).

Step 5: Synthesis of Compound 2-6

To dioxane (3 mL) and water (0.6 mL) were added compound I-7 (140 mg, 503.39 μmol), borate 2-5A (178.39 mg, 553.73 μmol), and potassium carbonate (139.14 mg, 1.01 mmol), and then [1,1'-bis(diphenylphosphino)ferrocene]dichloropalladium(II) ($Pd(dppf)Cl_2$) (36.83 mg, 50.34 μmol) was added thereto. The mixture was then stirred and reacted in a 105° C. oil bath for 15 hours under nitrogen atmosphere. The reaction mixture was dried by rotary evaporation to obtain a crude product. The crude product was purified by silica gel column chromatography (ethyl acetate/petroleum ether=0 to 25%) to obtain compound 2-6. $^1$H NMR: (400 MHZ, $CHCl_3$) δ: 7.87 (d, J=8.0 Hz, 1H), 7.28 (d, J=1.6 Hz, 1H), 7.10 (dd, J=1.6, 8.0 Hz, 1H), 5.0 (s, 2H), 3.3 (s, 3H), 3.55 (s, 3H), 3.23 (t, J=14.4 Hz, 2H), 3.13 (t, J=6.8 Hz, 2H), 2.39-2.24 (m, 2H).

Step 6: Synthesis of Compound 2-7

Compound 2-6 (105 mg, 266.90 μmol) was dissolved in tetrahydrofuran (2 mL), and then an aqueous solution of lithium hydroxide monohydrate (2 M, 533.80 μL) was added thereto. The resulting reaction mixture was stirred at 25° C. (room temperature) for 15 hours. The reaction mixture was dried at 40° C. by rotary evaporation to remove tetrahydrofuran. The residue was added with 2 M hydrochloric acid to adjust the pH to between 2 and 3, resulting in the precipitation of a large amount of solid. Ethyl acetate (50 mL) was added thereto, and the mixture was stirred. The ethyl acetate was then separated and the mixture was dried by rotary evaporation to obtain compound 2-7, and the crude product was directly used in the next step.

Step 7: Synthesis of Compound of Formula (I)

Compound 2-7 (105 mg, 276.77 μmol) was dissolved in methanol (1 mL), and hydrochloric acid (60.55 mg, 1.66 mmol, 59.36 μL) was added thereto. The reaction mixture turned turbid, and was stirred at 25° C. for 3 hours. The reaction mixture was dried by rotary evaporation at 40° C., and the resulting residue was purified by preparative HPLC (chromatographic column: Venusil ASB Phenyl 150*30 mm*5 um; mobile phase: [water (0.05% HCl)-ACN]; ACN %: 60% to 90%, 9 minutes) to obtain the compound of formula (I). $^1$H NMR (400 MHZ, $CD_3OD$) δ: 8.00 (d, J=8.0 Hz, 1H), 7.13-7.04 (m, 2H), 3.35-3.32 (m, 2H), 3.12 (t, J=7.2 Hz, 2H), 2.45-2.30 (m, 2H); MS (ESI) m/z: 334.02 [M−H].

Example 3: Preparation of Crystal Form B of Compound of Formula (I)

Figure 4:
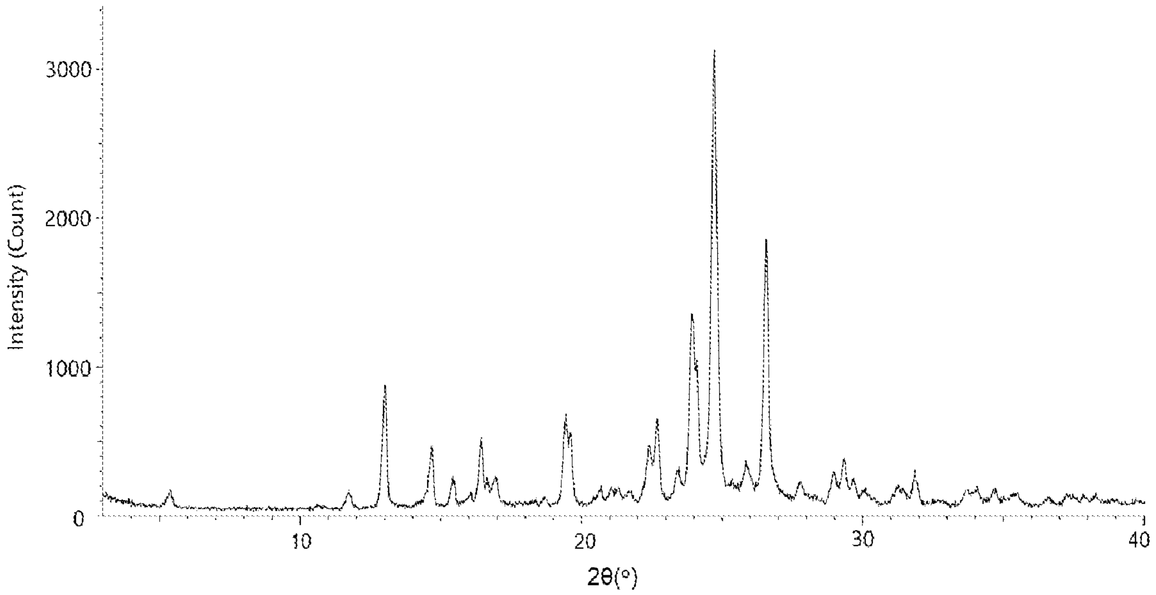
FIG. 4 is a Cu-Kα radiation XRPD pattern of the crystal form B of the compound of formula (I).

To dichloromethane (1 mL) was added the crystal form A (20 mg, 0.06 mmol) of the compound of formula (I), and the mixture was stirred at 25° C. for 120 hours. The mixture was filtered. The filter cake was dried under reduced pressure at 50° C. for 2 to 5 hours to obtain the crystal form B of the compound of formula (I). The XRPD pattern of the crystal form B is shown in FIG. 4.

Example 4: Preparation of Crystal Form C of Compound of Formula (I)

Figure 5:
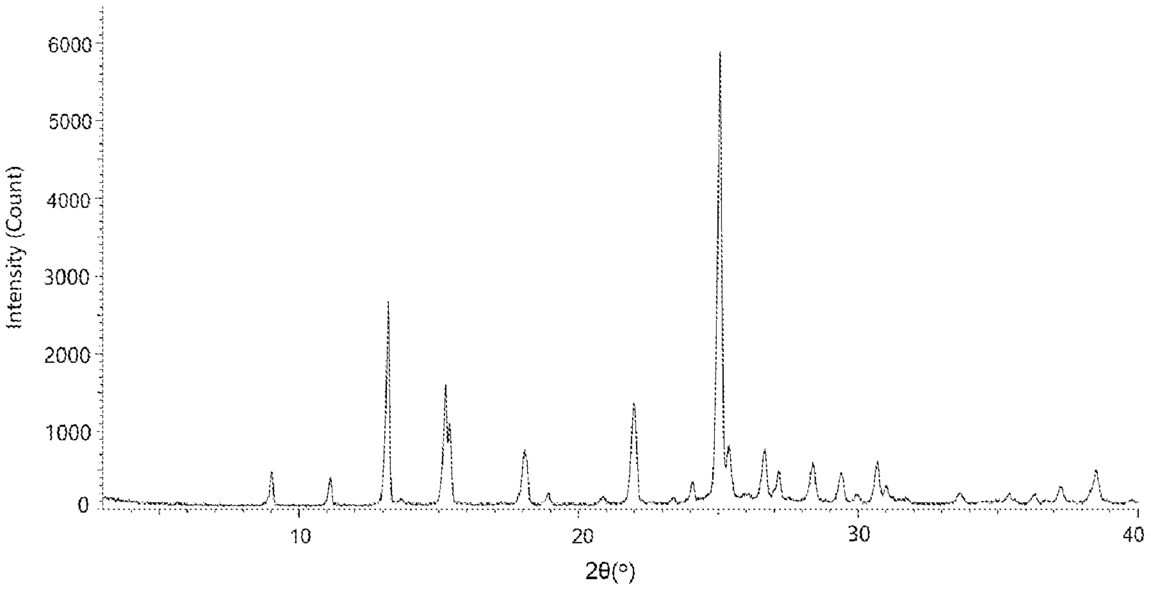
FIG. 5 is a Cu-Kα radiation XRPD pattern of the crystal form C of the compound of formula (I).
Figure 6:
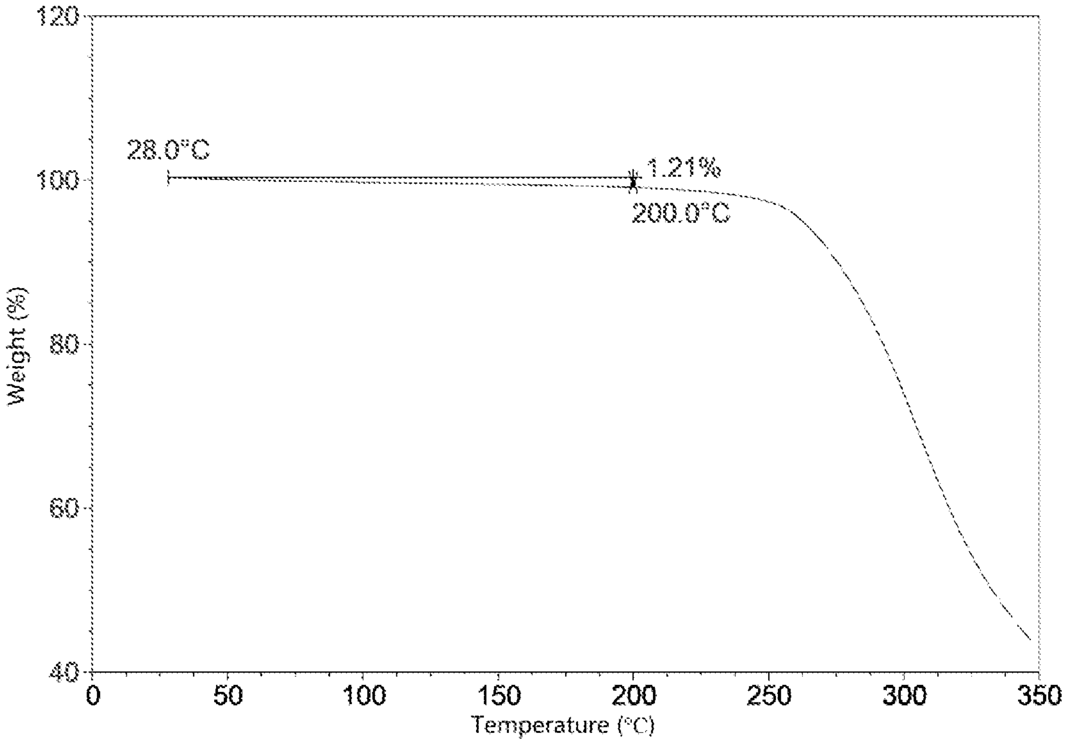
FIG. 6 is a TGA pattern of the crystal form C of the compound of formula (I).
Figure 7:
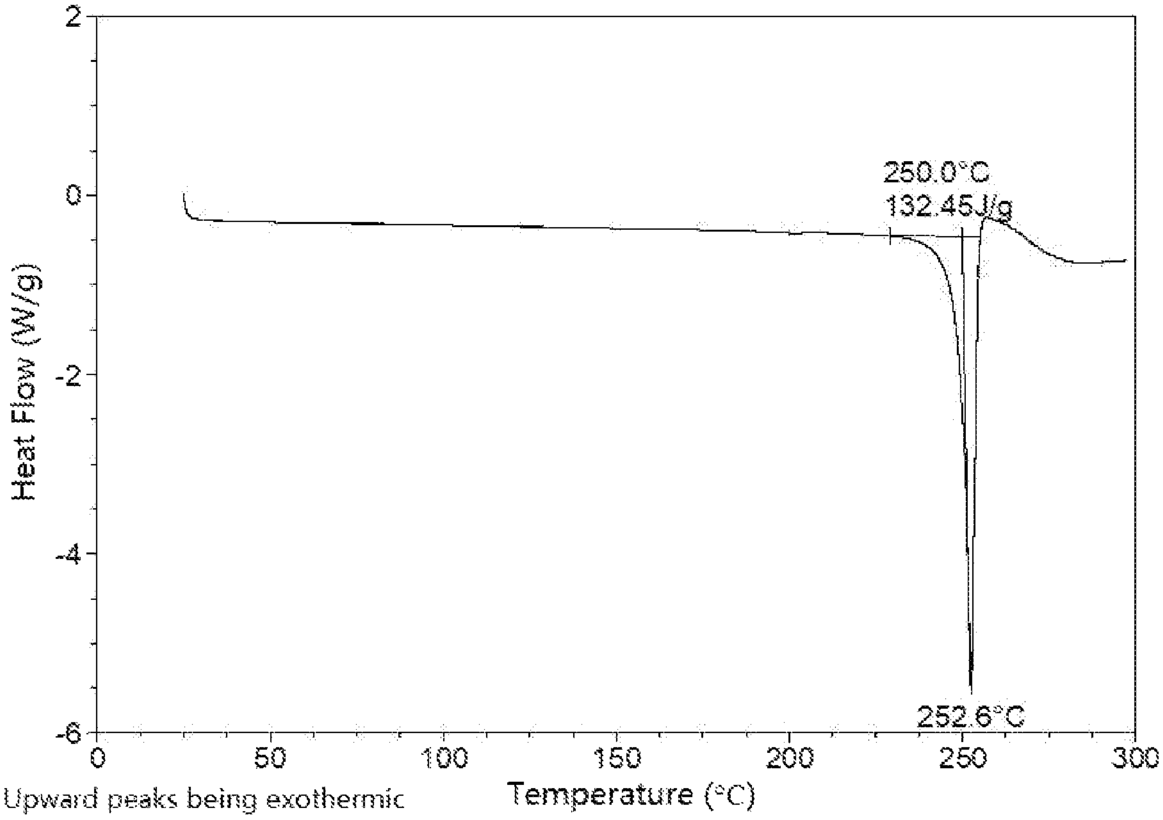
FIG. 7 is a DSC pattern of the crystal form C of the compound of formula (I).

To a mixture solvent of ethyl acetate (5 mL) and heptane (5 mL) was added the crystal form A (1.0 g, 2.98 mmol) of the compound of formula (I), then the mixture was stirred at 25° C. for 72 hours. The mixture was filtered. The filter cake was dried under reduced pressure at 45° C. for 2 hours to obtain the crystal form C of the compound of formula (I). The XRPD pattern of the crystal form C is shown in FIG. 5, the TGA pattern thereof is as shown in FIG. 6, and the DSC pattern thereof is shown in FIG. 7.

Example 5: Preparation of Crystal Form D of Compound of Formula (I)

Figure 8:
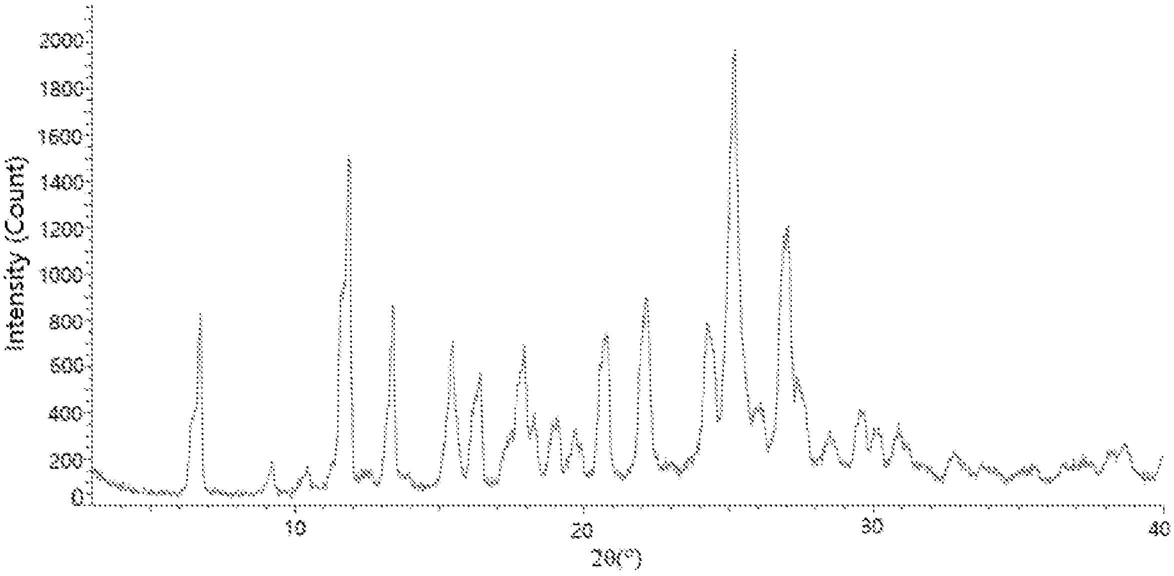
FIG. 8 is a Cu-Kα radiation XRPD pattern of the crystal form D of the compound of formula (I).
Figure 9:
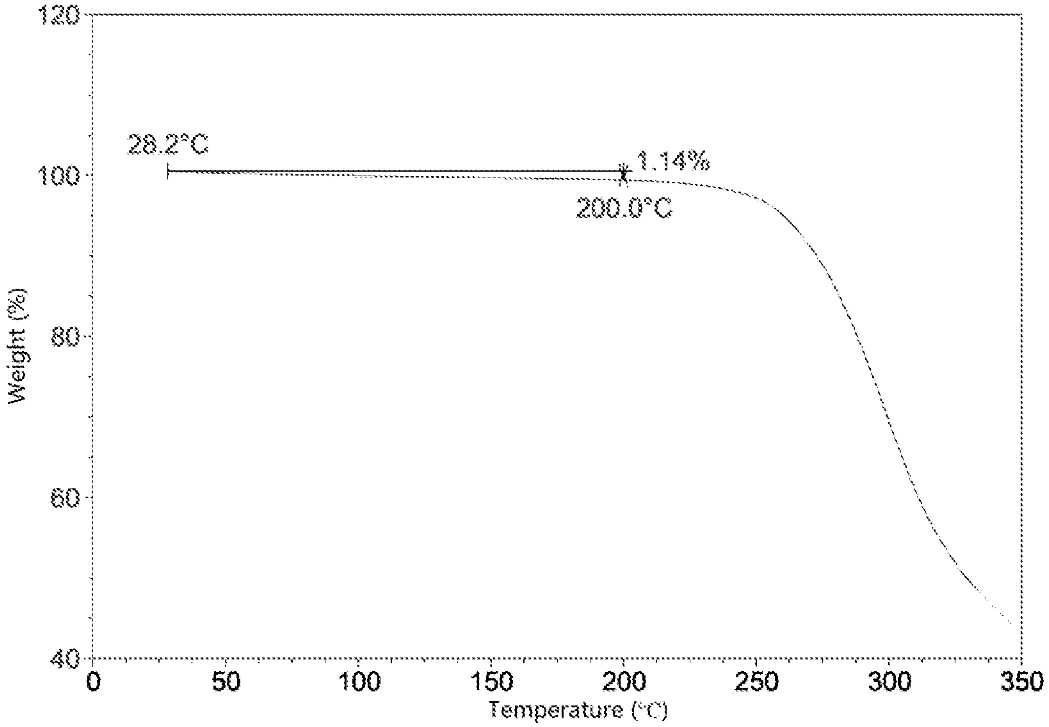
FIG. 9 is a TGA pattern of the crystal form D of the compound of formula (I).
Figure 10:
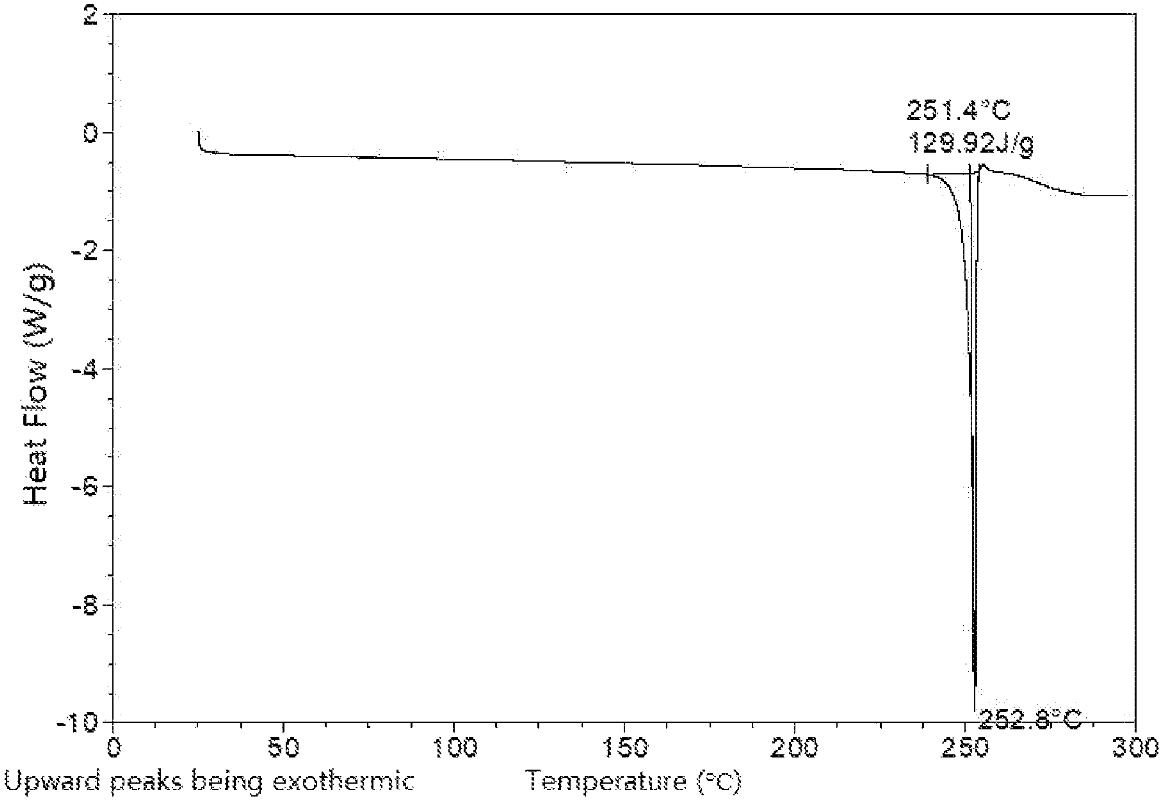
FIG. 10 is a DSC pattern of the crystal form D of the compound of formula (I).

To a mixture solvent of tetrahydrofuran (0.4 mL) and water (0.4 mL) was added 20 mg of the weighed crystal form A of the compound of formula (I). The mixture was stirred at 50° C. till all solids were dissolved, cooled to 13° C., and stirred for 72 hours. The mixture was filtered. The filter cake was dried under reduced pressure at 45° C. for 2 hours to obtain the crystal form D of the compound of formula (I). The XRPD pattern of the crystal form D is shown in FIG. 8, the TGA pattern thereof is shown in FIG. 9, and the DSC pattern thereof is shown in FIG. 10.

Example 6: Preparation of Crystal Form E of Compound of Formula (I)

Figure 11:
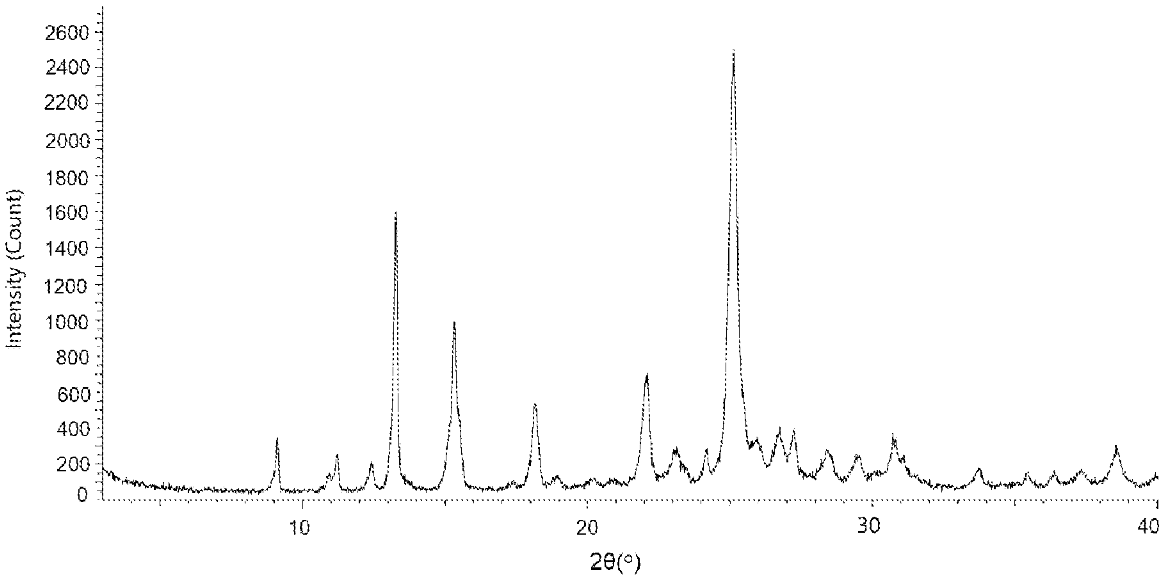
FIG. 11 is a Cu-Kα radiation XRPD pattern of the crystal form E of the compound of formula (I).
Figure 12:
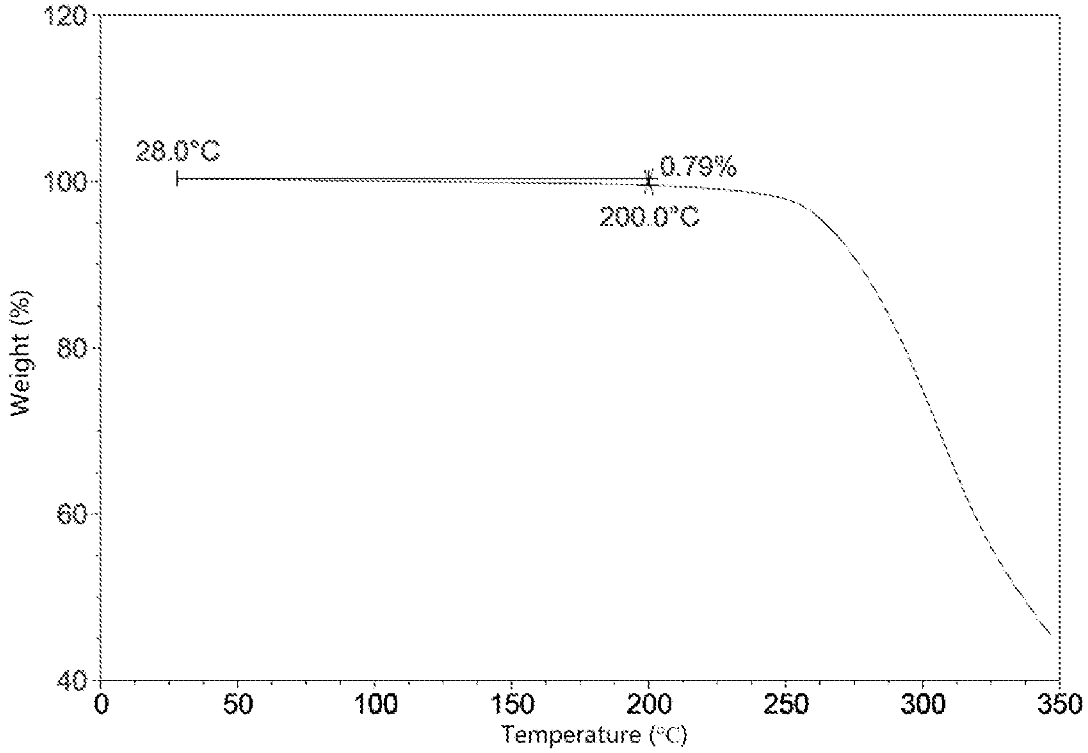
FIG. 12 is a TGA pattern of the crystal form E of the compound of formula (I).
Figure 13:
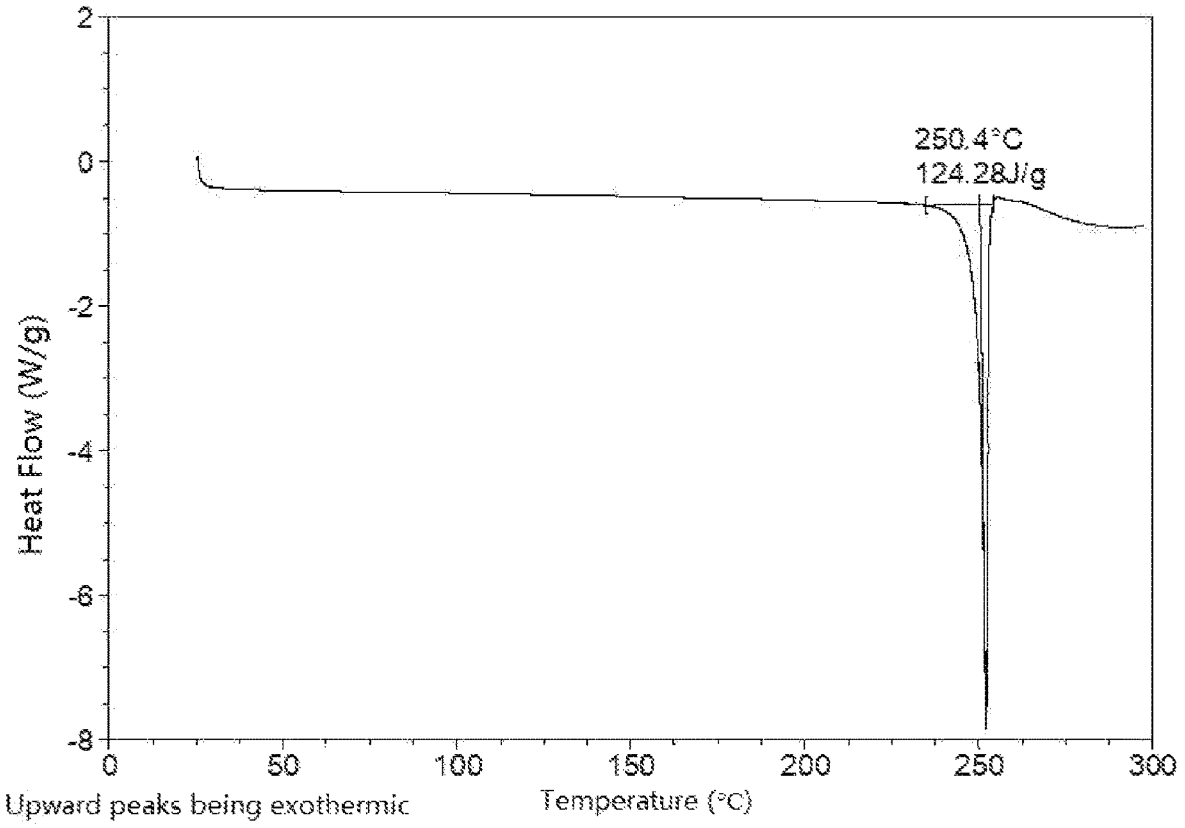
FIG. 13 is a DSC pattern of the crystal form E of the compound of formula (I).

To a mixture solvent of tetrahydrofuran (3.3 mL) and water (6.6 mL) was added the crystal form A (1.0 g, 2.98 mmol) of the compound of formula (I). The resulting mixture was stirred at 25° C. for 72 hours. The mixture was filtered. The filter cake was dried under reduced pressure at 45° C. for 2 hours to obtain the crystal form E of the compound of formula (I). The XRPD pattern of the crystal form E is shown in FIG. 11, the TGA pattern thereof is shown in FIG. 12, and the DSC pattern thereof is shown in FIG. 13.

Example 7: Study on Hygroscopicity of Crystal Form C of Compound of Formula (I)

Experimental Materials:

DVS Intrinsic dynamic vapor sorption analyzer

Experimental Methods:

10 to 30 mg of the crystal form C of the compound of formula (I) was taken and placed in a DVS sample tray for testing.

Figure 14:
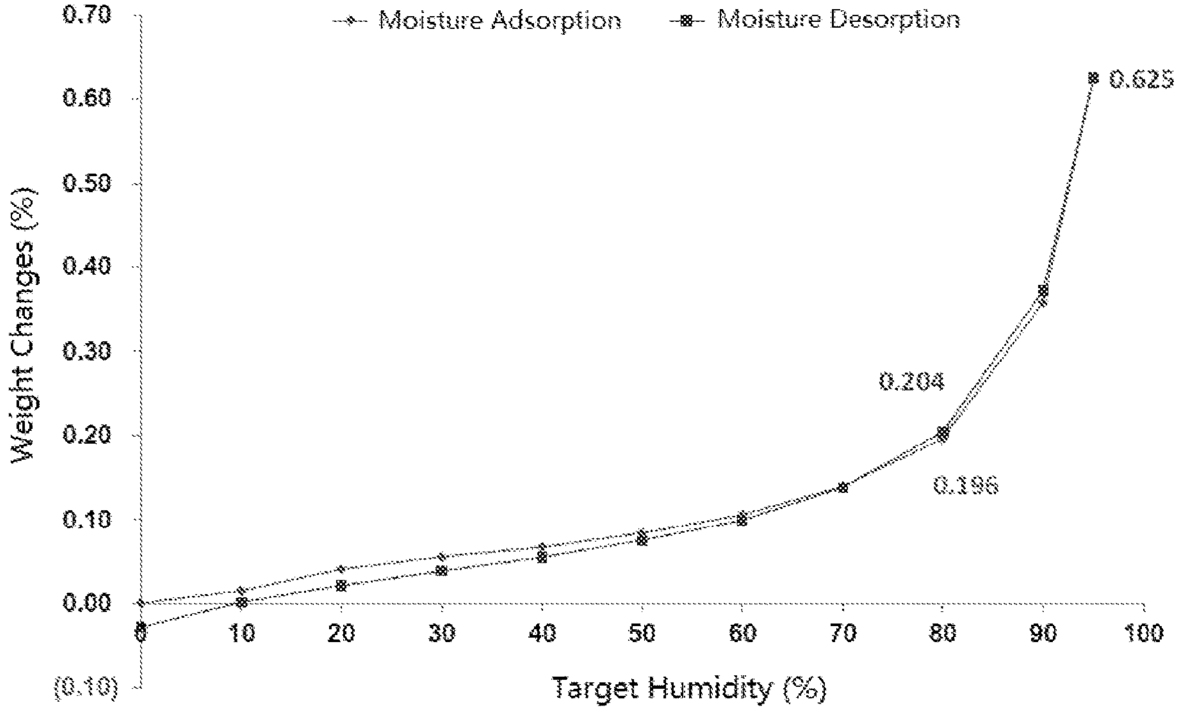
FIG. 14 is a DVS pattern of the crystal form C of the compound of formula (I).

Experimental Results:

The DVS spectrum for the crystal form C of the compound of the formula (I) is as shown in FIG. 14, with ΔW equals 0.196%.

Experimental Conclusion:

The compound of formula (I) in crystal form C exhibits no hygroscopicity, with a hygroscopic weight gain of 0.196% at 25° C. and 80% RH.

Example 8: Test on Solid-State Stability of Crystal Form C of Compound of Formula (I)

Based on the "Guideline for Stability Testing of Pharmaceutical Ingredients and Formulations" (Chinese Pharmacopoeia 2015 Edition, General Rule 9001), the stability of the compound of formula (I) in crystal form C was investigated under high temperature (60° C., open), high humidity (room temperature/relative humidity of 92.5%, open), and strong light exposure (5000 1×, sealed).

Twelve portions of the compound of formula (I) in crystal form C were weighed in parallel, each portion being approximately 1.5 g, and placed in flat weighing bottles (70*35 mm) or disposable petri dishes, spread into a thin layer. They were separately placed under stability conditions of high temperature (60° C.), high humidity (25° C./92.5% humidity), combined high temperature and high humidity (40° C./75% humidity), and light exposure. For the sample placed under high temperature and high humidity, the bottle was sealed with aluminum foil, with small holes punctured in the aluminum foil to ensure that the samples could fully contact the ambient air; the sample placed under strong light exposure was sealed with a quartz glass cap. The samples placed under high temperature (60° C.) and high humidity (92.5% humidity, room temperature) were taken for testing on the 5th and 10th days (appearance, related substances, and content). The samples placed under combined high temperature and high humidity (40° C./75% humidity) were taken for testing in the 1st, 2nd, and 3rd months (appearance, related substances, and content). The samples placed under light exposure conditions were taken for testing when the total illuminance reached $1.2\times10^6$ Lux•hr. The test results were compared with the initial test results on day 0, and the test results are shown in Table 7 below:

TABLE 7

Test results for solid-state stability of compound of formula (I)

| Test conditions | Time points | Related substances | Content |
|---|---|---|---|
| — | 0 days | 98.84% | 98.1% |
| High temperature (60° C., open-top) | 5 days | 98.94% | 98.5% |
| | 10 days | 98.95% | 98.3% |
| | 30 days | 98.87% | 98.1% |
| High humidity (25° C./relative humidity of 92.5%, open-top) | 5 days | 98.90% | 97.9% |
| | 10 days | 98.90% | 97.9% |
| | 30 days | 98.80% | 97.9% |
| Light exposure (total illuminance: $1.2 \times 10^6$ Lux · hr/near ultraviolet: 200 w · hr/$m^2$) | 5 days | 98.89% | 97.6% |
| | 10 days | 98.91% | 98.0% |
| 40° C., relative humidity of 75%, open-top | 1M | 98.83% | 97.8% |
| | 2M | 99.02% | 97.8% |
| | 3M | 98.86% | 97.8% |

Conclusion: The compound of formula (I) in crystal form C shows good stability under the influencing factors of high temperature, high humidity, strong light exposure, and accelerated conditions.

Bioassay Data:

Experimental Example 1: Inhibitory Activity Test Against Xanthine Oxidase

1. Experimental Purpose

To evaluate the level of inhibition on xanthine oxidase activity by the compound.

2. Reagents

The main reagents used in this study include xanthine (Sigma, Catalog Number: X4002-1G, Batch Number: SLBB5664V) and xanthine oxidase (Sigma, Catalog Number: X4376-5UN, Batch Number: SLBQ1518V).

3. Instruments

The major instrument used in this study is a multimodel microplate reader.

4. Experimental Methods:

1) To the compound background control well and HPE (with 100% inhibition rate activity) positive control well was added 50 μL of Dulbecco's Phosphate-Buffered Saline (DPBS).

2) 2 U/mL of xanthine oxidase was diluted with DPBS, resulting in a concentration of 0.04 U/mL, and to the compound activity test well and ZPE (with 0% inhibition rate activity) negative control well was added 50 μL of xanthine oxidase.

3) The compound was serially diluted using a 3-fold gradient across 8 data points with DMSO, and then further diluted with DPBS, with 50 μL added to each well in triplicate. To each HPE (100% inhibition rate) positive control well and ZPE (0% inhibition rate) negative control well were added 50 μL of DPBS.

4) 200 mM of xanthine was diluted with DPBS to 300 μM. To each well was added 100 μL of xanthine, and the reaction was allowed to proceed at room temperature for 30 minutes, resulting in a final concentration of 0.01 U/mL of xanthine oxidase and a final concentration of 0.5% DMSO in each well. The HPE (100% inhibition rate activity) positive control well contained xanthine but did not contain xanthine oxidase. The ZPE (0% inhibition rate activity) negative control well contained both xanthine and xanthine oxidase. The compound background control well contained various concentrations of the compound and xanthine but did not contain xanthine oxidase.

5) The absorbance values were measured at 290 nm using a spectrophotometer.

6) Data analysis: The inhibition rate of xanthine oxidase for each well was calculated using the following formula:

$$\text{inhibition rate}\,\% = \left(1 - \frac{OD_{test\ sample} - OD_{compound\ control}}{OD_{ZPE} - OD_{HPE}}\right) * 100\%$$

$OD_{test\ sample}$ refers to the optical density value of the compound activity test wells, which contained the compound, xanthine, and xanthine oxidase;

$OD_{compound\ control}$ refers to the background optical density value for different concentrations of the test compound wells, which contained the compound and xanthine, but not xanthine oxidase;

$OD_{ZPE}$ is the average optical density value of the zero inhibition activity control well, which contained 0.5% DMSO, xanthine, and xanthine oxidase;

$OD_{HPE}$ is the average optical density value of the 100% inhibition activity control well, which contained 0.5% DMSO and xanthine, but not xanthine oxidase.

7) Using GraphPad Prism software, the inhibition rate data (inhibition rate %) of the compounds was subjected to nonlinear curve fitting analysis with the log(agonist) vs. response—Variable slope method, leading to the determination of the $IC_{50}$ value for the compounds, and the fitting equation is as follows:

$$Y = \text{Bottom} + (\text{Top} - \text{Bottom})/\left(1 + 10\hat{\ }((\text{Log}IC_{50} - X) * HillSlope)\right)$$

5. Experimental Results

The experimental results are shown in Table 8.

TABLE 8

Results of anthine oxidase inhibition activity test for compounds

| Compound No. | XO $IC_{50}$ (nM) |
|---|---|
| Compound of formula (I) | 20.7 |

Conclusion: The compound of the present disclosure exhibits favorable inhibitory activity against xanthine oxidase.

Experiment Example 2: Testing Inhibitory Activity of Compound on Uric Acid Uptake 1. Experimental Purpose The present study utilized the human Urat1 stable transfected cell line to evaluate the inhibitory activity of the test compound on uric acid uptake.

2. Experimental Materials 2.1 Cell line

The human Urat1 stable transfected cell line was constructed by Wuxi APPTEC (Shanghai) Co., Ltd. The human Urat1 stable transfected cell line (Urat1-MDCK) was obtained by transfecting the MDCK cells with the human Urat1 gene, followed by G418 selection. The cell line was cultured in MEM containing 10% fetal bovine serum (FBS), 100 U/mL penicillin, 100 g/mL streptomycin, 2 mM L-glutamine, 1% non-essential amino acids, and 250 g/mL G418.

2.2 Reagents

The main reagents used in the present study included 14C-uric acid (ARC, catalog number: ARC-0513, batch number: 200122).

2.3 Instruments

The main instrument used in the present study was a liquid scintillation analyzer (Perkin Elmer, Tri-Carb 4910TR).

3. Experimental Methods:

3.1 Cell plating 3.1.1 The Urat1-MDCK cells cultured in T150 cell culture flasks were digested with 0.25% trypsin, and then diluted with fresh culture medium, resulting in a suspension of 200,000 cells/mL.

3.1.2 The cells were seeded into a 48-well cell culture plate, with 0.5 mL per well, resulting in a final density of 100,000 cells/well.

3.1.3 The cell culture plate was placed in a 37° C. incubator with 5% $CO_2$ and cultured overnight.

3.2 Compound treatment and testing:

3.2.1 The compound was diluted in DMSO at a 5-fold gradient for 4 points, with the diluted concentrations being 200 times the final testing concentration. The compound was then diluted 10-fold with HBSS buffer. 3.2.2 The 10 mM 14C-uric acid concentrated stock solution was diluted to 1 mM using HBSS buffer.

3.2.3 After overnight incubation of the cell culture plate, the cell culture medium was removed from the plate, and the cells were washed with HBSS buffer three times, after which, to each well 90 μL of HBSS buffer was added.

3.2.4 To each well was added 5 μL of the diluted compound, and the cells were placed in a 37° C., 5% $CO_2$ incubator for 20 minutes. Each well contained 0.5% of DMSO. The test compound (10 μM) was used as a control of 100% inhibition rate, and 0.5% DMSO was used as a control of 0% inhibition rate.

3.2.5 To each well of the cell plate was added 5 μL of the diluted 14C-uric acid, with a final concentration of 50 μM for uric acid in each well. The cells were placed in a 37° C., 5% $CO_2$ incubator for 15 minutes. The cells were then washed three times with pre-cooled HBSS buffer.

3.2.6 To each well was added 150 μL of 0.1 M NaOH to lyse the cells for 10 minutes.

3.2.7 The cell lysate was collected into liquid scintillation testing vials, with an additional 2 mL of scintillation fluid added to each vial for testing.

3.2.8 The 14C content of each sample was detected using a liquid scintillation analyzer.

3.2.9 Data analysis:

$$\text{Inhibition rate}\,\% = (HC - CPD)/(HC - LC) \times 100\% \; *$$

*CPD represents the radioactive signal value for the compound well;

HC represents the average radioactive signal value for the 0% inhibition control well;

LC represents the average radioactive signal value for the 100% inhibition control well.

3.2.10 In the GraphPad Prism software, nonlinear regression is performed using the log(inhibitor) vs. response—Variable slope method. The dose-response curve is fitted according to the following formula, and the $IC_{50}$ and $IC_{90}$ values for the compound are determined.

$$Y = \text{Bottom} + (\text{Top} - \text{Bottom})/\left(1 + 10\hat{}((\text{Log}IC_{50} - X) * HillSlope)\right)$$

4. Experimental Results:

The experimental results are shown in Table 9.

TABLE 9

| Inhibitory activity of compound on uric acid uptake | |
|---|---|
| Compound No. | $IC_{50}$ (μM) |
| Compound of formula I | 2.24 |

Conclusion: The compound of the present disclosure exhibits good inhibitory activity on uric acid uptake.

Experimental Example 3: Study of Hepatic Metabolic Stability (HMS) in Liver Cells 1. Experimental Purpose To test the metabolic stability of the test compound in human and rat liver cells.

2. Experimental Materials 2.1 Test Compound (10 mM), controls: 7-Ethoxycoumarin (30 mM), 7-Hydroxycoumarin (control, 30 mM)

2.2 Cells

Cell information is shown in Table 10.

TABLE 10

| Cell information | | |
|---|---|---|
| Liver cells | Cell Viability | Supplier Cat No. |
| Rat liver cells | 85% | BioreclamationIVTM00005 |
| Human liver cells | 84% | Bioreclamation IVTX008001 |

2.3 Buffer system:

Thawing medium: Williams Medium E, which contained 5% fetal bovine serum and 30% Percoll solution, along with other auxiliary agents.

Incubation medium: Williams Medium E (devoid of phenol red), which contained 2 mM L-glutamine and 25 mM HEPES.

Termination solution: acetonitrile, which contained 200 ng/ml of tolbutamide and labetalol as internal standards.

Dilution solvent: ultrapure water

3. Experimental methods

1) A 30 mM solution was prepared by dissolving a precise amount of the positive control compound in dimethyl sulfoxide (DMSO).

2) In a 96-well plate, the 10 mM test compound and 30 mM positive control compound were diluted to 1 mM and 3 mM, respectively, using DMSO.

3) Acetonitrile was used to further dilute the 1 mM test compound and 3 mM positive control compound to quantification solutions with final concentrations of 100 μM and 300 μM, respectively.

4) The stored cells were thawed, separated, and suspended in culture mediums. These cells were then diluted to a concentration of 0.5×10^6 cells/mL using pre-warmed culture mediums.

5) In the 96-well plate, 198 μL of the pre-warmed cell suspension was added.

6) To a pre-labeled set of a 96-well plate was transferred 100 μL of the termination solution (acetonitrile containing 200 ng/ml of tolbutamide and 200 ng/ml of labetalol as internal standards).

7) In duplicate, 2 μL of 100 μM test compound or 300 μM positive control solution was added to each well of the 96-well plate.

8) The TO samples were mixed for approximately one minute to produce a homogeneous suspension, followed by the immediate transfer of 20 μL of each sample to wells containing 100 μL of ice-cold termination solution, and they were mixed.

9) All plates were incubated at 37° C. in a 95% humidified incubator with 5% $CO_2$, and the reaction was initiated with a constant shaking at approximately 600 rpm.

10) At 15, 30, 60, and 90 minutes, samples were mixed, and then 20 μL from each sample was transferred at each time point to wells containing 100 μL of ice-cold termination solution, and they were mixed.

11) Medium control (MC) sample plates for T0 and T90 were prepared by adding the same components as in the other wells, excluding the cell suspension, and were labeled as TO-MC and T90-MC. The final concentration table was generated.

12) At each corresponding time point, the reaction was terminated by removing the plates from the incubator and mixing them with 100 μL of ice-cold termination solution.

13) Immediate vortexing of the plates was performed at 500 rpm on a platform shaker for 10 minutes. Subsequently, all sample plates were centrifuged at 3220×g for 20 minutes at 4° C.

14) After centrifugation, 35 μL of supernatant per well from the sample plates was transferred to another set of pre-labeled 96-well plates containing 70 μL of ultrapure water.

15) The analytical plates were sealed and stored at 4° C. until LC-MS-MS analysis.

Through the following formula, the residual rates for the test compound and the control compound were calculated.

$$\text{residual rate}(\%) = \frac{\begin{array}{c}\text{peak area ratio (compound/internal standard)}\\ \text{at any given time point}\end{array}}{\begin{array}{c}\text{peak area ratio (compound/internal standard)}\\ \text{at minute 0}\end{array}} \times 100\%$$

The elimination rate constant k for the test compound and control compound in hepatocytes was calculated by plotting the logarithm of the residual rate against time. The half-life ($T_{1/2}$) and intrinsic clearance rate ($CL_{int}$) were determined based on the elimination rate constant k. The formula is as follows:

$$T_{1/2} = 0.693/k$$

$$CL_{int\,(hep)} = k/\text{cell count per milliliter (million cells/mL)}$$

$$CL_{int\,(liver)} = CL_{int\,(hep)} \times \text{liver-to-body weight ratio} \times \text{number of hepatocytes per gram of liver}$$

Parameters for each species in the formula are shown in Table 11 below:

TABLE 11

Parameters for each species

| Species | Liver-to-body weight ratio (g/kg) | Hepatic blood flow rate ($Q_h$) (mL/min/kg) | Number of Hepatocytes (number of hepatocytes per gram of liver) |
|---|---|---|---|
| Rat | 40 | 55.2 | $117 \times 10^6$ |
| Human | 20 | 20.7 | $139 \times 10^6$ |

4. Experimental Results

The results are shown in Table 12.

TABLE 12

Intrinsic clearance rates of compounds in human and rat liver

| Compound No. | Hepatic intrinsic clearance rates (mL/min/Kg) Human | Rat |
|---|---|---|
| Compound of formula (I) | 31.8 | 188.4 |

Conclusion: The compound of the present disclosure exhibits moderate clearance in human liver cells and high clearance in rat liver cells.

Experimental Example 4: MDR1 Membrane Permeability Test

1. Experimental Purpose:

MDR1-MDCK II cells are Madin-Darby canine kidney cells transfected with the human MDR1 gene, enabling stable high expression of P-gp. The purpose of the present study is to test the bidirectional permeability of the compound across the MDR1-MDCK II cell model and evaluate its potential for efflux transport.

2. Cell Culture:

MDR1-MDCK II cells (sourced from Piet Borst at the Netherlands Cancer Institute) were seeded on polyethylene terephthalate (PET) membranes in a 96-well insert system at a density of $2.5\times10^5$ cells/mL. The cells were cultured until they formed a confluent monolayer over 4-7 days.

3. Experimental Methods

Test compounds were diluted in transport buffer (HBSS containing 10 mM Hepes with DMSO, pH 7.4) to a concentration of 2 μM (DMSO<1%) and were applied to either the apical or basolateral side of the cell monolayer. Replicate measurements of the test compound were made in both the A-to-B and B-to-A directions. Digoxin was also tested in both directions at a concentration of 10 μM, while Nadolol and Metoprolol were tested at 2 μM in the A-to-B direction. The plate was incubated in a $CO_2$ incubator at 37±1° C. with a 5% $CO_2$ saturated humidity environment for 2.5 hours without shaking. Additionally, efflux ratios for each compound were measured, and both test and reference compounds were quantified, based on the peak area ratio of the analyte to IS by LC/MS/MS analysis. After the transport assay, the integrity of the cell monolayer was determined using a Lucifer Yellow exclusion assay. The buffer was removed from both the apical and basolateral chambers, followed by the addition of 75 μL of 100 μM fluorescein in transport buffer to the apical chamber and 250 μL of transport buffer to both the apical and basolateral chambers. The plate was incubated at 37° C. with 5% $CO_2$ and under saturated humidity for 30 minutes without shaking. After 30 minutes of incubation, 20 μL of fluorescein sample was extracted from the apical chamber and 60 μL of transport buffer was added thereto. Then, 80 μL of fluorescein sample was collected from the basolateral side of the cell. The relative fluorescence units (RFU) of fluorescein were measured at 425/528 nm (excitation/emission) using an Envision microplate reader.

4. Data Calculation

The apparent permeability coefficient (Papp, cm/s), efflux ratio, and recovery rate were calculated using the following formulas:

The apparent permeability coefficient (Papp, cm/s) is calculated as follows:

$$P_{app} = (dC_r/d_t) \times V_r/(A \times C_0)$$

Where dC/d, is the cumulative concentration of the compound at the receiver end per unit time (M/s); $V_r$ is the volume of the receiver solution (the volumes of the apical and basolateral solutions are 0.075 mL and 0.250 mL, respectively); A is the relative surface area of the cell monolayer (0.0804 $cm^2$); and $C_0$ is the initial concentration of the test compound (nM) or the peak area ratio of the control.

The efflux ratio is calculated using the following formula:

$$\text{efflux ratio} = P_{app}(BA)/P_{app}(AB)$$

The recovery rate is calculated using the following formula:

$$\%\ \text{recovery rate} = 100 \times [(V_r \times C_r) + (V_d \times C_d)]/(V_d \times C_0)$$

Where $C_0$ is the initial concentration (nM) of the test compound or the peak area ratio of the control; $V_a$ is the volume at the dosing end (the apical side is 0.075 mL, and the basolateral side is 0.250 mL); $C_0$ and $C_1$ are the final concentrations (nM) of the test compound at the dosing and receiving ends, respectively, or the peak area ratio of the control.

The percentage of fluorescein in the basolateral wells is calculated using the following formula:

$$\%\ \text{Lucifer Yellow} = \frac{V_{Basolateral} \times RFU_{Basolateral}}{V_{Apical} \times RFU_{Apical} + V_{Basolateral} \times RFU_{Basolateral}} \times 100$$

In which $RFU_{Apical}$ and $RFU_{Basolateral}$ are the Relative Fluorescence Units of fluorescein in the apical and basolateral wells, respectively; $V_{Apical}$ and $V_{Basolateral}$ are the volumes of apical and basolateral wells, respectively (0.075 mL and 0.25 mL). The percentage of fluorescein should be less than 2%.

5. Experimental Results

The results are shown in Table 13.

TABLE 13

Data on membrane permeability of compound in MDR1 cells

| Compound No. | $P_{app}$ (AB) ($10^{-6}$ cm/s) | $P_{app}$ (BA) ($10^{-6}$ cm/s) | Efflux ratio |
|---|---|---|---|
| Compound of formula (I) | 26.42 | 6.63 | 0.25 |

Conclusion: The compound of the present disclosure is highly permeable.

Experimental Example 5: Testing for Cytochrome P450 Isoenzyme Inhibitory Activity 1. Experimental Purpose To determine the inhibitory activity of the test compound against different subtypes of human cytochrome P450 isoenzymes.

2. Experimental Methods

Test compounds, standard inhibitors (at 100× final concentration), and mixed substrate working solutions were prepared; the microsomes (purchased from Corning Inc.) stored at −80° C. were taken out and thawed. To the corresponding wells were added 20 μL of the test compound and standard inhibitor solutions. Meanwhile, 20 μL of the respective solvent was added to the No Inhibitor Control (NIC) and blank control wells. Next, 20 μL of mixed substrate solution was added to the corresponding wells, except the blank wells where 20 μL of phosphate buffer (PB) was added. A human liver microsome solution was prepared (immediately returned to the fridge after the date of use was marked). Then, 158 μL of this solution was added to all the wells. The sample plate was placed in a 37° C. water bath for pre-incubation. A co-enzyme factor (NADPH) solution was then promptly prepared. After 10 minutes, 20 μL of NADPH solution was added to all wells. The sample plate was shaken to mix and placed back into a 37° C. water bath for an additional 10 minutes of incubation. At the respective time points, the reaction was terminated by adding 400 μL of cold acetonitrile solution (internal standard at 200 ng/ml of tolbutamide and labetalol). The sample plate was mixed thoroughly and was then centrifuged at 4000 rpm for 20 minutes to precipitate proteins. 200 μL of the supernatant was taken and mixed with 100 μL of water, after which it was sent for LC/MS/MS analysis.

3. Experimental Results

The results are shown in Table 14.

TABLE 14

$IC_{50}$ values of the compound for inhibition of P450 isoenzymes

| | Cytochrome P450 isoenzymes $IC_{50}$ (μM) | | | | |
|---|---|---|---|---|---|
| Compound No. | CYP1A2 | CYP2C9 | CYP2C19 | CYP2D6 | CYP3A4-M |
| Compound of formula (I) | >50 | 18.1 | >50 | >50 | >50 |

Conclusion: The compound of the present disclosure exhibits extremely low inhibitory activity against CYP1A2, CYP2C19, CYP2D6, and CYP3A4-M, and moderate inhibitory activity against CYP2C9.

Example 6: Pharmacokinetics in SD Rats In Vivo

1. Experimental Purpose:

To test the pharmacokinetics of the compound in SD rats in vivo

2. Experimental Materials:

Sprague Dawley rats (male, 180-350 g, 6 to 10 weeks of age, Beijing Vital River).

3. Experimental Methods:

The compound was mixed with 5% DMSO/10% Solutol/85% water, stirred, and vortexed to prepare a clear solution of 0.6 mg/mL for administration in the injection group. The solution was then filtered through a micropore membrane for later use. The compound was mixed with 5% DMSO/10% Solutol/85% water, stirred, and vortexed to prepare a clear solution of 1 mg/mL for oral administration. Six male SD rats were divided into two groups. In the first group, animals received a single intravenous injection at a dose of 3 mg/kg, using 5% DMSO/10% Solutol/85% water as the solvent, with a dosing volume of 5 mL/kg. In the second group, animals received a single oral gavage dose of the test compound at 10 mg/kg. The oral solvent was 5% DMSO/10% Solutol/85% water, with a dosing volume of 10 mL/kg. Whole blood samples were collected at 0 (oral gavage group only), 0.083 (intravenous injection group only), 0.25, 0.5, 1, 2, 4, 8, and 24 hours post-administration. Whole blood was centrifuged at 3200 g for 10 minutes at 4° C. to obtain plasma. The concentrations of the compound and uric acid (in the oral gavage group only) in the plasma were measured using the LC/MS/MS method. Pharmacokinetic parameters such as peak concentration, time to reach peak concentration, clearance rate, half-life, area under the curve, and bioavailability were calculated using Phoenix WinNonlin software.

The results are shown in Table 15 below:

TABLE 15

Pharmacokinetic data of compound of formula (I) in rats

| 2.89 mpk/intravenous injection | | | | | |
|---|---|---|---|---|---|
| | $C_0$ (μM) | $T_{1/2}$ (hr) | $Vd_{ss}$ (L/kg) | Cl (mL/min/kg) | $AUC_{0\text{-}inf}$ (μM · hr) |
| Compound of formula (I) | 96.6 | 3.74 | 0.32 | 3.59 | 41.8 |
| **8.58 mpk/oral** | | | | | |
| | $C_{max}$(μM) | $T_{max}$ (hr) | $T_{1/2}$ (hr) | $AUC_{0\text{-}inf}$ (μM · hr) | Bioavailability (%) |
| Compound of formula (I) | 27.5 | 0.5 | 2.47 | 86.6 | 62.1 |

Conclusion: The compounds of the present disclosure have favorable pharmacokinetic properties and high oral bioavailability, where $C_0$ represents the initial concentration, $T_{1/2}$ is the elimination half-life, $Vd_{ss}$ is the steady-state apparent volume of distribution, Cl is the total clearance rate, $AUC_{0\text{-}last}$ is the area under the plasma concentration-time curve from time 0 to the last quantifiable time point, $AUC_{0\text{-}inf}$ is the area under the plasma concentration-time curve from time 0 extrapolated to infinity, $C_{max}$ is the peak concentration, and $T_{max}$ is the time to reach peak concentration.

What is claimed is:

1. A crystal form C of a compound of formula (I), wherein the crystal form C has an X-ray powder diffraction pattern comprising characteristic diffraction peaks at the following 2θ angles: 13.20±0.20°, 15.26±0.20°, 18.08±0.20°, 21.99±0.20°, 25.07=0.20°, 25.38±0.20°, 26.66±0.20°, and 30.70=0.20°, (I)

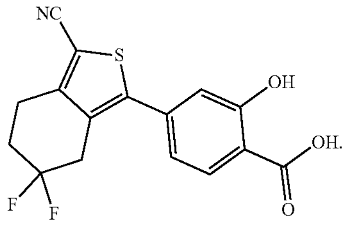

2. The crystal form C according to claim 1, wherein the X-ray powder diffraction pattern thereof has characteristic diffraction peaks at the following 2θ angles: 9.03±0.20°, 13.20=0.20°, 15.26=0.20°, 18.08±0.20°, 21.99-0.20°, 25.07=0.20°, 25.38=0.20°, 26.66=0.20°, 28.38±0.20°, 29.41±0.20°, 30.70±0.20°, and 38.53-0.20°.

3. The crystal form C according to claim 1, wherein the X-ray powder diffraction pattern thereof has characteristic diffraction peaks at the following 2θ angles: 13.20°, 15.26°, 18.08°, 21.99°, 25.07°, 25.38°, 26.66°, and 30.70°.

4. The crystal form C according to claim 1, wherein the X-ray powder diffraction pattern thereof has characteristic diffraction peaks at the following 2θ angles: 5.66°, 9.03°, 11.13°, 13.20°, 13.70°, 15.26°, 17.25°, 18.08°, 18.92°, 20.88°, 21.99°, 23.41°, 24.09°, 25.07°, 25.38°, 25.99°, 26.66°, 27.17°, 28.38°, 29.41°, 29.98°, 30.70°, 31.02°, 31.72°, 33.67°, 35.40°, 36.35°, 36.74°, 37.26°, 38.53°, and 39.80°.

5. The crystal form C according to claim 1, wherein the crystal form C has an XRPD pattern basically as shown in FIG. 5.

6. The crystal form C according to claim 1, wherein the crystal form C has a thermogravimetric analysis curve with a weight loss of 1.21% at 200° C.±3° C.

7. The crystal form C according to claim 6, wherein the crystal form C has a TGA pattern as shown in FIG. 6.

8. The crystal form C according to claim 1, wherein the crystal form C has a differential scanning calorimetry curve comprising an endothermic peak with an onset at 250.0° C.±2° C.

9. The crystal form C according to claim 8, wherein the crystal form C has a DSC pattern as shown in FIG. 7.

10. A crystal form E of a compound of formula (I), wherein the crystal form E has an X-ray powder diffraction pattern comprising characteristic diffraction peaks at the following 2θ angles: 9.11±0.20°, 12.43=0.20°, 13.28=0.20°, 15.34±0.20°, 18.16±0.20°, 22.06=0.20°, 23.15±0.20°, and 25.14±0.20°,

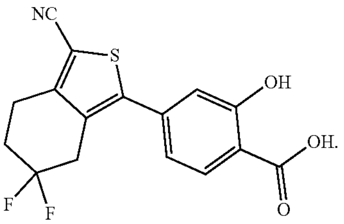

(I)

11. The crystal form E according to claim 10, wherein the X-ray powder diffraction pattern thereof has characteristic diffraction peaks at the following 2θ angles: 9.11=0.20°, 11.21±0.20°, 12.43±0.20°, 13.28±0.20°, 15.34±0.20°, 18.16=0.20°, 22.06±0.20°, 23.15±0.20°, 25.14±0.20°, 25.97±0.20°, 26.75±0.20°, and 27.25±0.20°.

12. The crystal form E according to claim 10, wherein the X-ray powder diffraction pattern thereof has characteristic diffraction peaks at the following 2θ angles: 9.11°, 12.43°, 13.28°, 15.34°, 18.16°, 22.06°, 23.15°, and 25.14°.

13. The crystal form E according to claim 10, wherein the X-ray powder diffraction pattern thereof has characteristic diffraction peaks at the following 2θ angles: 9.11°, 10.94°, 11.21°, 12.43°, 13.28°, 15.34°, 17.39°, 18.16°, 18.94°, 20.18°, 20.95°, 22.06°, 23.15°, 23.35°, 24.19°, 25.14°, 25.97°, 26.75°, 27.25°, 28.45°, 29.49°, 30.16°, 30.82°, 33.74°, 35.45°, 36.39°, 37.34°, and 38.57°.

14. The crystal form E according to claim 10, wherein the crystal form E has an XRPD pattern basically as shown in FIG. 11.

15. The crystal form E according to claim 10, wherein the crystal form E has a thermogravimetric analysis curve with a weight loss of 0.79% at 200° C.±3° C.

16. The crystal form E according to claim 15, wherein the crystal form E has a TGA pattern as shown in FIG. 12.

17. The crystal form E according to claim 10, wherein the crystal form E has a differential scanning calorimetry curve comprising an endothermic peak with an onset at 250.4° C.±2° C.

18. The crystal form E according to claim 17, wherein the crystal form E has a DSC pattern as shown in FIG. 13.

19. A method for treating gout and hyperuricemia in a subject in need thereof, comprising administering the crystal form C according to claim 1 to the subject.

20. A method for treating gout and hyperuricemia in a subject in need thereof, comprising administering the crystal form E according to claim 10 to the subject.

* * * * *